United States Patent
Ikeda

(10) Patent No.: US 10,349,819 B2
(45) Date of Patent: Jul. 16, 2019

(54) ENDOSCOPE DEVICE, METHOD FOR OPERATING ENDOSCOPE DEVICE, AND COMPUTER-READABLE RECORDING MEDIUM

(71) Applicant: OLYMPUS CORPORATION, Tokyo (JP)

(72) Inventor: Yuichi Ikeda, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 322 days.

(21) Appl. No.: 15/368,283

(22) Filed: Dec. 2, 2016

(65) Prior Publication Data
US 2017/0079508 A1 Mar. 23, 2017

Related U.S. Application Data

(63) Continuation of application No. PCT/JP2015/064520, filed on May 20, 2015.

(30) Foreign Application Priority Data

Jun. 25, 2014 (JP) .................................. 2014-130481

(51) Int. Cl.
*A61B 1/005* (2006.01)
*A61B 1/00* (2006.01)
(Continued)

(52) U.S. Cl.
CPC .............. *A61B 1/0055* (2013.01); *A61B 1/00* (2013.01); *A61B 1/00006* (2013.01);
(Continued)

(58) Field of Classification Search
CPC ........................ A61B 1/00006; A61B 1/00055; A61B 1/008; A61B 1/005; A61B 1/0051; A61B 1/0053; G02B 23/24
See application file for complete search history.

(56) References Cited

U.S. PATENT DOCUMENTS 4,930,494 A * 6/1990 Takehana ........... A61B 1/00147
600/145
5,060,632 A * 10/1991 Hibino ............... A61B 1/00039
348/65
(Continued)

FOREIGN PATENT DOCUMENTS

JP 6-181882 A 7/1994
JP 3752328 B2 3/2006
(Continued)

OTHER PUBLICATIONS

International Search Report dated Aug. 18, 2015 received in PCT/JP2015/064520.

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

An endoscope device includes: an insertion unit having segments continuously provided along an axial direction of the insertion unit and configured to be inserted into a lumen; a state quantity calculating unit configured to calculate a state quantity of each segment; variable rigidity portions provided for each segment to allow bending rigidity of each segment to be variable; an origin specifying unit configured to specify an origin segment among the segments in setting a segment range indicating which segment the bending rigidity is to be changed or in setting the bending rigidity, based on the state quantity of each segment; and an operation controller configured to: set the segment range or set the bending rigidity of each segment, based on the origin segment; and decrease bending rigidities of two or more continuously provided segments based on the set segment range or on the set bending rigidity.

20 Claims, 20 Drawing Sheets

(51) Int. Cl.
*G02B 23/24* (2006.01)
*A61B 1/008* (2006.01)
(52) U.S. Cl.
CPC ............ *A61B 1/008* (2013.01); *A61B 1/0051* (2013.01); *A61B 1/0053* (2013.01); *A61B 1/00055* (2013.01); *G02B 23/24* (2013.01)

(56) References Cited

U.S. PATENT DOCUMENTS

| | | | | |
|---|---|---|---|---|
| 6,468,203 B2* | 10/2002 | Belson | ................. | A61B 1/0053 600/145 |
| 6,610,007 B2* | 8/2003 | Belson | ................. | A61B 1/0053 600/146 |
| 6,858,005 B2* | 2/2005 | Ohline | ................. | A61B 1/0053 600/139 |
| 6,974,411 B2* | 12/2005 | Belson | ................. | A61B 1/00078 600/114 |
| 6,984,203 B2* | 1/2006 | Tartaglia | ............ | A61B 1/00147 600/114 |
| 7,338,505 B2* | 3/2008 | Belson | ................. | A61B 1/00147 600/146 |
| 8,827,894 B2* | 9/2014 | Belson | ................. | A61B 1/0053 600/114 |
| 9,220,398 B2* | 12/2015 | Woodley | ............ | A61B 1/0053 |
| 9,345,390 B2* | 5/2016 | Matsuo | ............ | A61B 1/00071 |
| 9,427,282 B2* | 8/2016 | Belson | ................. | A61B 1/0051 |
| 2002/0019582 A1* | 2/2002 | Takase | ............ | A61B 1/00071 600/140 |
| 2002/0062062 A1* | 5/2002 | Belson | ................. | A61B 1/0053 600/146 |
| 2002/0082585 A1* | 6/2002 | Carroll | ............ | A61M 25/0041 604/528 |
| 2003/0032859 A1* | 2/2003 | Belson | ................. | A61B 1/00078 600/114 |
| 2003/0171650 A1* | 9/2003 | Tartaglia | ............ | A61B 1/00147 600/114 |
| 2005/0020901 A1* | 1/2005 | Belson | ................. | A61B 1/0051 600/407 |
| 2007/0038028 A1* | 2/2007 | Uchimura | .......... | A61B 1/00071 600/144 |
| 2007/0066866 A1* | 3/2007 | Noguchi | ............. | A61B 1/0005 600/102 |
| 2007/0149852 A1* | 6/2007 | Noguchi | ............. | A61B 1/00147 600/144 |
| 2007/0161856 A1* | 7/2007 | Belson | ............... | A61B 1/00151 600/114 |
| 2009/0024141 A1* | 1/2009 | Stahler | .................. | A61B 34/71 606/130 |
| 2009/0099420 A1* | 4/2009 | Woodley | ............ | A61B 1/0053 600/142 |
| 2009/0138025 A1* | 5/2009 | Stahler | .................. | A61B 34/71 606/130 |
| 2009/0216083 A1* | 8/2009 | Durant | ................. | A61B 1/0055 600/130 |
| 2010/0160735 A1* | 6/2010 | Bakos | ................. | A61B 17/3417 600/141 |
| 2010/0168519 A1* | 7/2010 | Matsuo | ............. | A61B 1/00071 600/139 |
| 2011/0009698 A1* | 1/2011 | Ashida | ............. | A61B 1/00006 600/118 |
| 2011/0295065 A1* | 12/2011 | Gurusamy | ............. | A61B 1/008 600/114 |
| 2013/0041214 A1* | 2/2013 | Maahs | ............... | A61B 1/00179 600/104 |
| 2013/0096423 A1* | 4/2013 | Yamamoto | ......... | A61B 1/00006 600/424 |
| 2013/0178705 A1* | 7/2013 | Takeuchi | ............. | A61B 1/0051 600/144 |
| 2015/0065953 A1* | 3/2015 | Ducharme | ........ | A61M 25/0158 604/95.05 |
| 2016/0360951 A1* | 12/2016 | Hane | ...................... | G02B 23/26 |

FOREIGN PATENT DOCUMENTS

| | | | | |
|---|---|---|---|---|
| WO | WO-2005072445 A2 * | 8/2005 | ........... | A61B 1/0051 |
| WO | WO-2007033379 A2 * | 3/2007 | ......... | A61B 1/00154 |
| WO | WO-2008094949 A2 * | 8/2008 | ........... | A61B 1/0052 |
| WO | WO-2009097461 A1 * | 8/2009 | ........... | A61B 1/0051 |

* cited by examiner

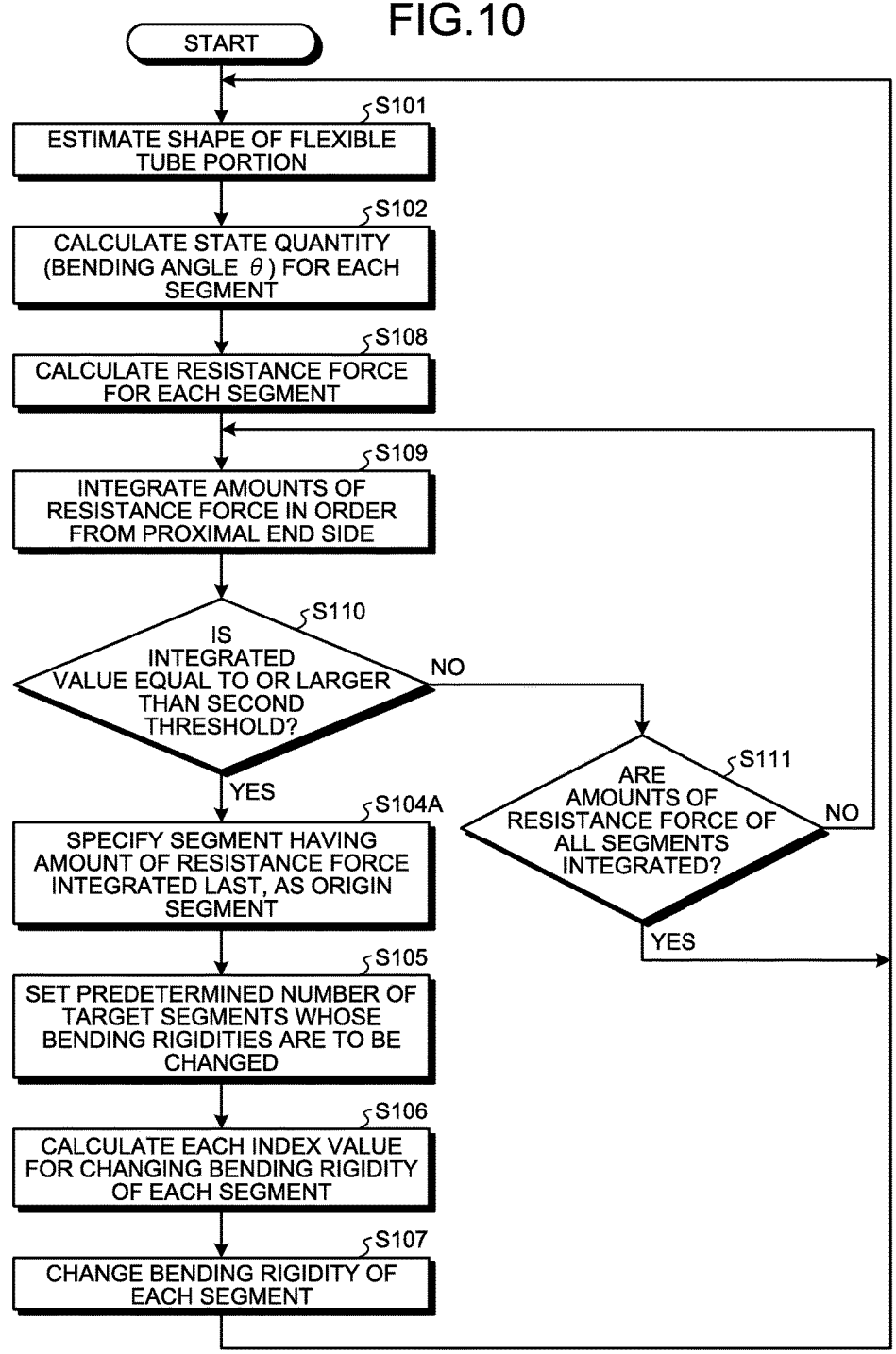

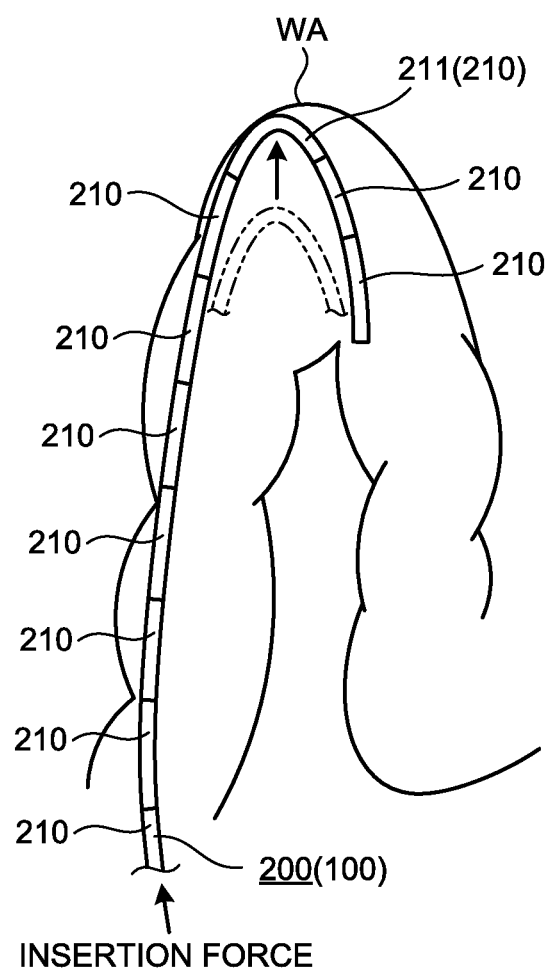

ENDOSCOPE DEVICE, METHOD FOR OPERATING ENDOSCOPE DEVICE, AND COMPUTER-READABLE RECORDING MEDIUM

CROSS REFERENCES TO RELATED APPLICATIONS

This application is a continuation of PCT international application Ser. No. PCT/JP2015/064520, filed on May 20, 2015 which designates the United States, incorporated herein by reference, and which claims the benefit of priority from Japanese Patent Application No. 2014-130481, filed on Jun. 25, 2014, incorporated herein by reference.

BACKGROUND

1. Technical Field

The disclosure relates to an endoscope device and a method for operating the endoscope device. The disclosure also relates to a computer-readable recording medium.

2. Related Art

Conventional techniques have been known in which an endoscope device with a flexible elongated insertion unit to be inserted into a living body (a lumen such as the large intestine) of a human and the like which observes the inside of the living body by using an image sensor provided at a distal end of the insertion unit is provided with a pressure sensor and a variable stiffness mechanism on the insertion unit (for example, refer to JP 3752328 B2).

The endoscope device disclosed in JP 3752328 B2 is provided with a plurality of pressure sensors and a plurality of variable stiffness mechanisms for each section (hereinafter, referred to as segment) arranged in an axial direction of the insertion unit. The endoscope device operates the variable stiffness mechanism of the segment to decrease stiffness of the segment (soften the segment) when the pressure sensor of a certain segment is pressed by a body cavity wall at the time of insertion of the insertion unit into the living body.

However, the endoscope device disclosed in JP 3752328 B2 may cause the following situation.

FIGS. 18A to 18C are schematic views for illustrating a conventional endoscope device 100. Specifically, FIGS. 18A to 18C sequentially illustrate a state of an insertion unit 200 when an operator of the insertion unit 200 applies insertion force to the insertion unit 200 of the endoscope device 100 inserted into the large intestine in a distal end direction.

As illustrated in FIG. 18A, suppose that the insertion unit 200 is inserted into the large intestine and a certain segment 211 (a segment 210 widely bent in FIG. 18A) of the insertion unit 200 abuts on a body cavity wall WA of a bent portion in the large intestine.

In this case, a pressure sensor of the segment 211 is pressed by the body cavity wall WA, so that the endoscope device 100 operates a variable stiffness mechanism of the segment 211 to decrease stiffness of the segment 211. As a result, a bending amount of the segment 211 further increases according to the amount of the insertion force applied by the operator to the insertion unit 200 as illustrated in FIG. 18B.

Herein, the pressure sensor of the segment 210 other than the segment 211 is not pressed by the body cavity wall WA. That is to say, the stiffness of other segments 210 is not changed. Therefore, when the operator applies the insertion force to the insertion unit 200, the bending amount of the segment 211 increases but the bending amounts of other segments 210 do not increase and the segment 211 in an acute-angled shape pushes the body cavity wall WA as illustrated in FIG. 18C. That is to say, even when the insertion force is applied to the insertion unit 200, the shape of the segment 210 other than the segment 211 does not change, and the insertion force is merely converted to force to extend the large intestine (to push the body cavity wall WA). Hence, propulsion in the distal end direction is scarcely generated and it is not possible to pass through the bent portion of the large intestine. In addition, a subject may suffer pain by the push on the body cavity wall WA.

SUMMARY

In some embodiments, an endoscope device includes: an insertion unit having a plurality of segments continuously provided along an axial direction of the insertion unit and configured to be inserted into a lumen; a state quantity calculating unit configured to calculate a state quantity indicating a state of each of the plurality of segments; a plurality of variable rigidity portions provided for each of the plurality of segments to allow bending rigidity of each of the plurality of segments to be variable; an origin specifying unit configured to specify an origin segment among the plurality of segments in setting a segment range indicating which segment the bending rigidity is to be changed or in setting the bending rigidity, based on the state quantity of each of the plurality of segments; and an operation controller configured to operate the plurality of variable rigidity portions to change the bending rigidity of each of the plurality of segments. The operation controller is configured to: set the segment range indicating which segment the bending rigidity is to be changed among the plurality of segments or set the bending rigidity of each of the plurality of segments, based on the origin segment; and decrease bending rigidities of two or more continuously provided segments among the plurality of segments based on the set segment range or on the set bending rigidity.

In some embodiments, a method for operating an endoscope device is provided. The endoscope device includes: an insertion unit having a plurality of segments continuously provided along an axial direction of the insertion unit and configured to be inserted into a lumen; and a plurality of variable rigidity portions provided for each of the plurality of segments to allow bending rigidity of each of the plurality of segments to be variable. The method includes: calculating, by a state quantity calculating unit, a state quantity indicating a state of each of the plurality of segments; specifying, by an origin specifying unit, an origin segment in setting a segment range indicating which segment the bending rigidity is to be changed or in setting the bending rigidity, among the plurality of segments, based on the state quantity of each of the plurality of segments; setting, by an operation controller, the segment range indicating which segment the bending rigidity is to be changed among the plurality of segments, or setting the bending rigidity of each of the plurality of segments, based on the origin segment; and decreasing, by the operation controller, bending rigidities of two or more continuously provided segments among the plurality of segments based on the set segment range or on the set bending rigidity.

In some embodiments, provided is a non-transitory computer-readable recording medium with an executable program stored thereon for operating an endoscope device. The endoscope device includes: an insertion unit having a plurality of segments continuously provided along an axial direction of the insertion unit and configured to be inserted into a lumen; and a plurality of variable rigidity portions provided for each of the plurality of segments to allow bending rigidity of each of the plurality of segments to be variable. The program causes the endoscope device to execute: calculating, by a state quantity calculating unit, a state quantity indicating a state of each of the plurality of segments; specifying, by an origin specifying unit, an origin segment in setting a segment range indicating which segment the bending rigidity is to be changed or in setting the bending rigidity, among the plurality of segments, based on the state quantity of each of the plurality of segments; setting, by an operation controller, the segment range indicating which segment the bending rigidity is to be changed among the plurality of segments, or setting the bending rigidity of each of the plurality of segments, based on the origin segment; and decreasing, by the operation controller, bending rigidities of two or more continuously provided segments among the plurality of segments based on the set segment range or on the set bending rigidity.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 10 is a flowchart illustrating operation of the endoscope device illustrated in FIG. 9;

FIG. 18C is a schematic view for illustrating the conventional endoscope device.

DETAILED DESCRIPTION

Modes for carrying out the present invention (hereinafter, referred to as "embodiment(s)") will be hereinafter described with reference to the drawings. The present invention is not limited by the embodiments. The same reference signs are used to designate the same elements throughout the drawings.

First Embodiment

Schematic Configuration of Endoscope Device

Figure 1:
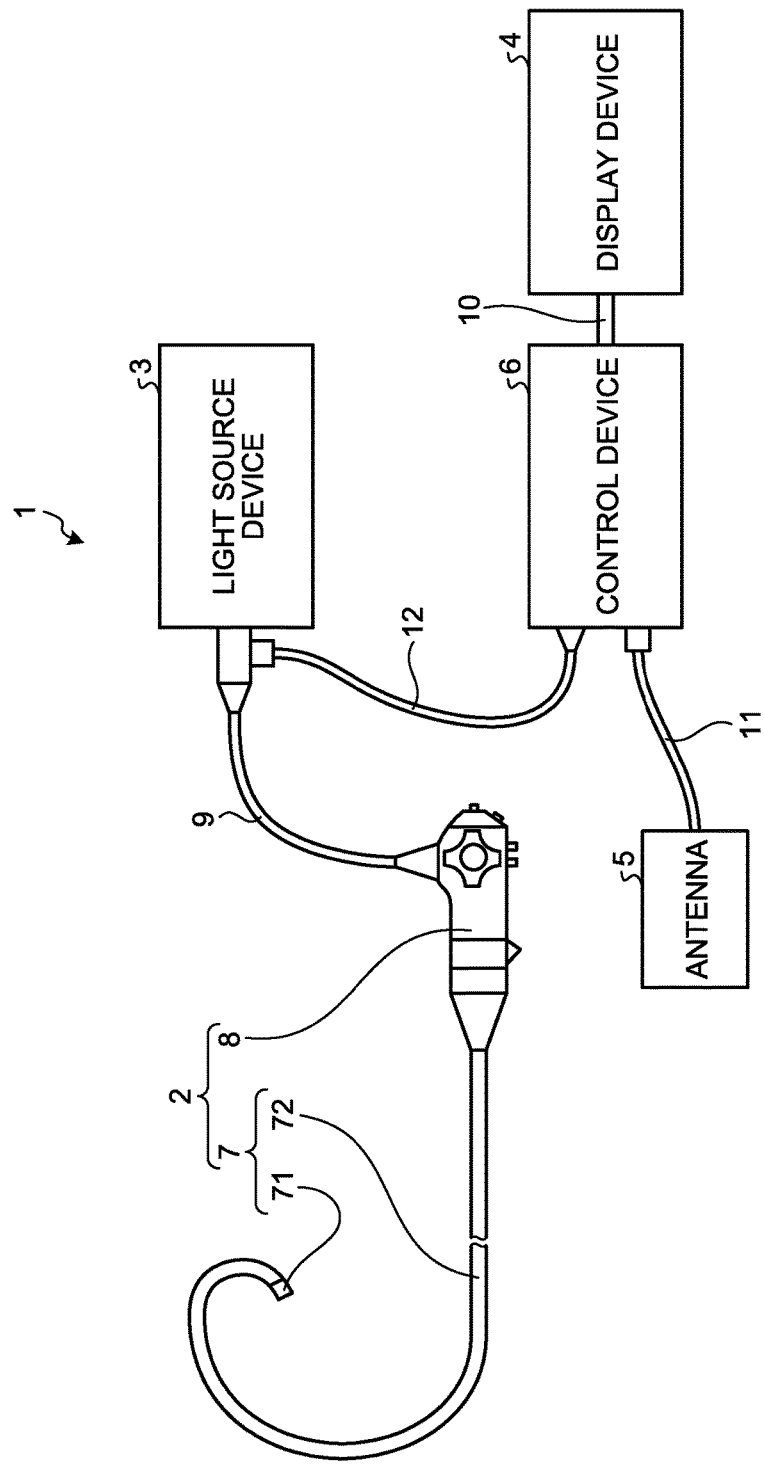
FIG. 1 is a block diagram of an endoscope device according to a first embodiment of the present invention.

FIG. 1 is a block diagram of an endoscope device 1 according to a first embodiment of the present invention.

The endoscope device 1 is a device used in a medical field which observes the inside of a living body (for example, a lumen such as the large intestine) of a human and the like. The endoscope device 1 is provided with an endoscope 2, a light source device 3, a display device 4, an antenna 5, and a control device 6 as illustrated in FIG. 1.

The endoscope 2 is configured to examine the inside of the living body to output a result of the examination. The endoscope 2 is provided with an insertion unit 7 and an operating unit 8 as illustrated in FIG. 1.

The insertion unit 7 which is flexible and having an elongated shape is configured to be inserted into the living body. The insertion unit 7 is provided with a distal end portion 71 and a flexible tube portion 72.

The distal end portion 71 is located at a distal end of the insertion unit 7. An illumination window (not illustrated) for illuminating the inside of the living body, an observation window (not illustrated) for observing the inside of the living body, an aperture (not illustrated) through which forceps being treatment tools and the like are inserted are provided on the distal end portion 71.

One end of a light guide (not illustrated) drawn in the endoscope 2 (the operating unit 8 and the insertion unit 7) is connected to the illumination window. That is to say, light emitted from the one end of the light guide irradiates the inside of the living body through the illumination window.

An imaging unit 73 (refer to FIG. 4) for capturing an image of the inside of the living body through the observation window under the control of the control device 6 is arranged in the distal end portion 71.

The imaging unit 73 is formed of an observation optical system (not illustrated) which condenses the light which irradiates the inside of the living body (an object image) through the observation window, an image sensor such as a charge coupled device (CCD) or a complementary metal oxide semiconductor (CMOS) (not illustrated) which receives the object image condensed (formed) by the observation optical system and converts the same to an electric signal, a signal processor (not illustrated) which performs signal processing (A/D conversion and the like) on the electric signal (an analog signal) from the image sensor to output an imaging signal and the like.

The flexible tube portion 72 is continuously provided on a proximal end side (a side closer to the operating unit 8 opposite to the distal end) of the distal end portion 71. The flexible tube portion 72 is formed of a plurality of segments 721 (refer to FIG. 2) arranged along a central axis Ax1 (refer to FIG. 2) of the insertion unit 7 and bending rigidity of each of a plurality of segments 721 may be independently changed under the control of the control device 6. Because of the bending rigidity of each of a plurality of segments 721 independently changing under the control of the control device 6, the flexible tube portion 72 is bendable according to a shape of a body cavity wall when this abuts on the body cavity wall in the living body.

A detailed configuration of the flexible tube portion 72 will be described later.

The operating unit 8 connected to a proximal end of the flexible tube portion 72 is a part with which an operator operates the endoscope 2 while holding the endoscope 2. Various switches for issuing a capturing instruction and the like are provided on the operating unit 8.

The light source device 3 is connected to the endoscope 2 through a universal code 9 as illustrated in FIG. 1.

Here, the above-described light guide and a signal cable which transmits a signal (an imaging signal, a control signal and the like) between the endoscope 2 and the control device 6 are embedded in the universal code 9.

That is, the light source device 3 to which the other end of the above-described light guide embedded in the universal code 9 is connected supplies the light for irradiating the inside of the living body to the other end of the light guide.

The display device 4 is connected to the control device 6 through a first signal cable 10 and displays images under the control of the control device 6.

The antenna 5 arranged around the living body into which the endoscope 2 is inserted detects a magnetic field generated by a source coil 722 (refer to FIG. 2) to be described later embedded in the flexible tube portion 72. The antenna 5 connected to the control device 6 through a second signal cable 11 outputs a detection signal obtained by the detection to the control device 6.

The control device 6 is connected to the signal cable embedded in the universal code 9 through a third signal cable 12. The control device 6 is connected to the display device 4 through the first signal cable 10. The control device 6 including a central processing unit (CPU) and the like integrally controls operation of the endoscope 2 and the display device 4 according to a program (also including an operation program) recorded in a memory (not illustrated).

A detailed configuration of the control device 6 will be described later.

Configuration of Flexible Tube Portion

Figure 2:
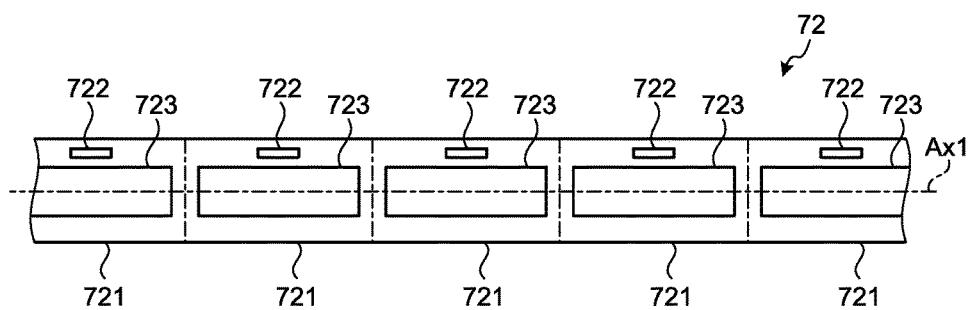
FIG. 2 is a schematic view illustrating an internal configuration of a flexible tube portion illustrated in FIG. 1.

FIG. 2 is a schematic view illustrating an internal configuration of the flexible tube portion 72.

The light guide and the signal cable drawn in the flexible tube portion 72 are not illustrated in FIG. 2.

The flexible tube portion 72 is formed of a plurality of segments 721 arranged along the central axis Ax1 and the source coil 722 and a variable stiffness element 723 are embedded in each segment 721 as illustrated in FIG. 2. The source coil 722 and the variable stiffness element 723 may be embedded in each of all the segments 721 or only in some segments 721.

The source coil 722 having a configuration in which a copper wire is wound around a magnetic material such as ferrite and permalloy is used for estimating a shape of the flexible tube portion 72. The source coil 722 to which an alternating-current signal is applied from the control device 6 through the signal cable (not illustrated) drawn in the flexible tube portion 72 generates the magnetic field around the source coil 722 (outputs positional information regarding a position of the source coil 722).

The source coil 722 corresponds to a position detecting unit.

Figure 3A:
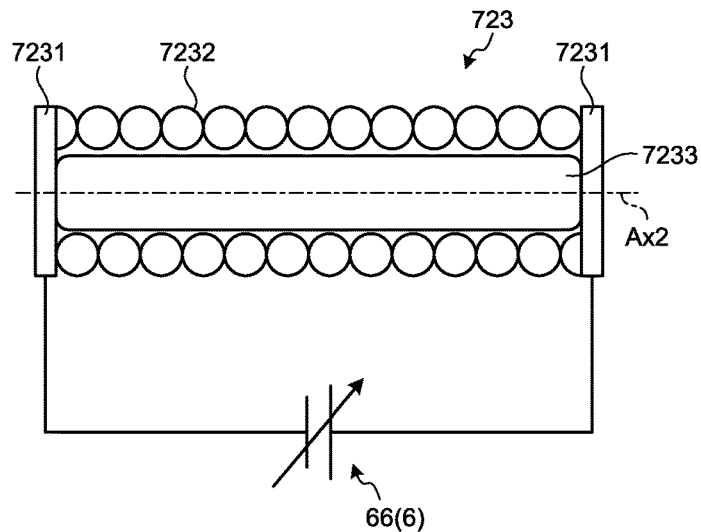
FIG. 3A is a schematic view illustrating a configuration of a variable stiffness element illustrated in FIG. 2.
Figure 3B:
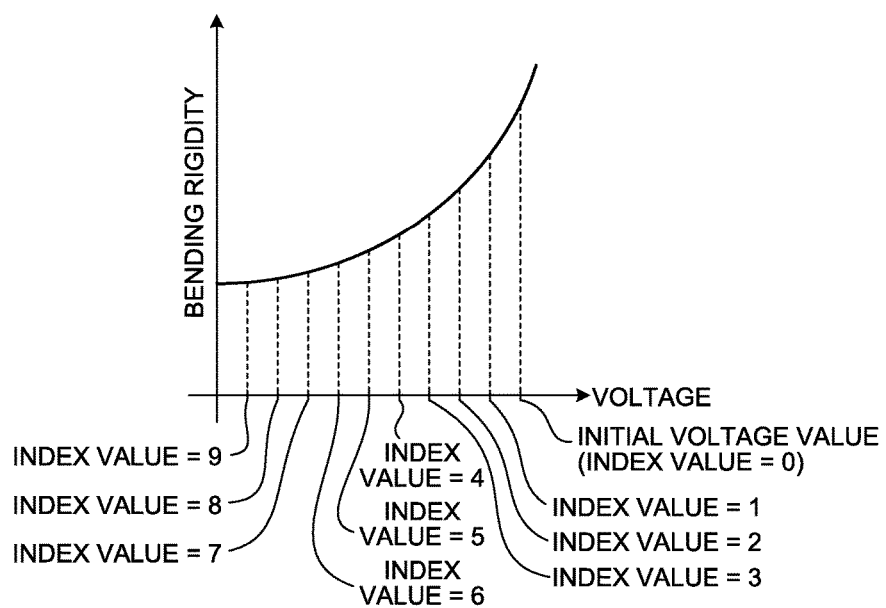
FIG. 3B is a graph illustrating characteristics of the variable stiffness element illustrated in FIG. 2.

FIG. 3A is a schematic view illustrating a configuration of the variable stiffness element 723. FIG. 3B is a graph illustrating characteristics of the variable stiffness element 723.

The variable stiffness element 723 is provided with a coil pipe 7232 on each of both ends of which an electrode 7231 is provided and a conductive polymer artificial muscle 7233 (hereinafter referred to as an electroactive polymer artificial muscle (EPAM) 7233) enclosed in the coil pipe 7232 as illustrated in FIG. 3A. The variable stiffness element 723 is embedded in the flexible tube portion 72 such that a central axis Ax2 of the coil pipe 7232 (FIG. 3A) is identical to or parallel to the central axis Ax1 of the insertion unit 7.

In the variable stiffness element 723, voltage is applied from the control device 6 to the electrode 7231 (EPAM 7233) through the signal cable (not illustrated) drawn in the flexible tube portion 72. Herein, the EPAM 7233 tends to enlarge a diameter thereof around the central axis Ax2 of the coil pipe 7232 when the voltage is applied thereto; however, enlargement of the diameter is regulated by the coil pipe 7232. Therefore, stiffness (bending rigidity) of the variable stiffness element 723 increases as a voltage value applied thereto increases as illustrated in FIG. 3B. That is to say, changing the stiffness of the variable stiffness element 723 also changes the bending rigidity of the segment 721 in which the variable stiffness element 723 is embedded.

The variable stiffness element 723 described above corresponds to a variable rigidity portion.

Configuration of Control Device

Figure 4:
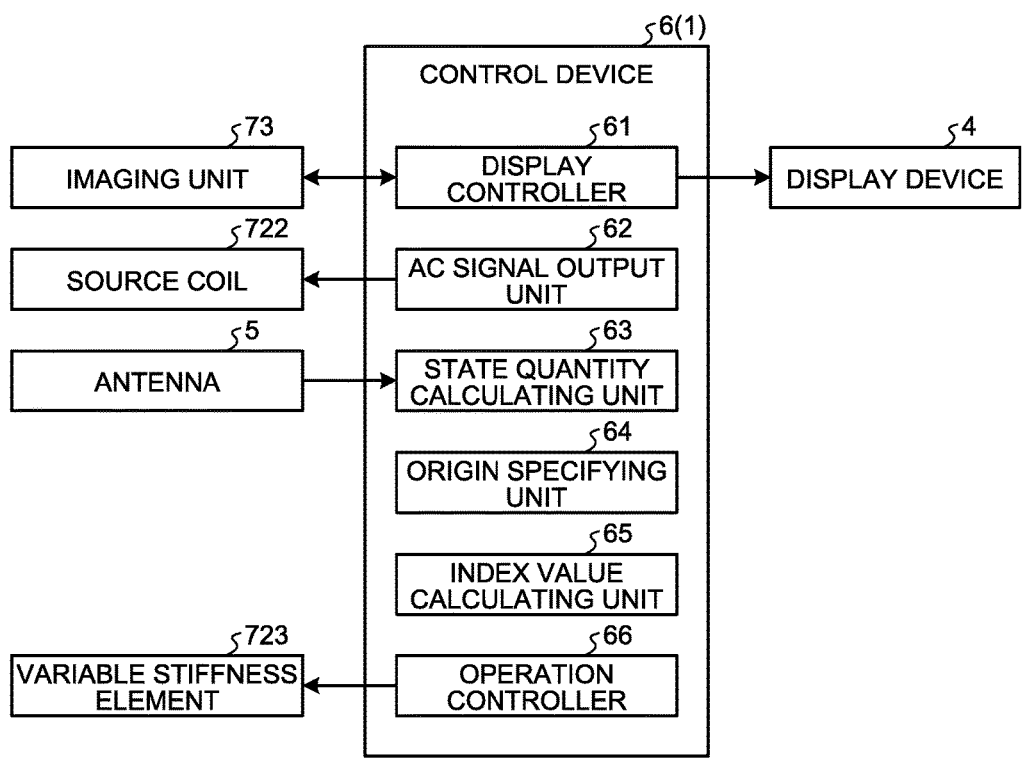
FIG. 4 is a block diagram illustrating a configuration of a control device illustrated in FIG. 1.

FIG. 4 is a block diagram illustrating a configuration of the control device 6.

The control device 6 is provided with a display controller 61, an AC signal output unit 62, a state quantity calculating unit 63, an origin specifying unit 64, an index value calculating unit 65, and an operation controller 66 as illustrated in FIG. 4.

The display controller 61 controls operation of the imaging unit 73 to obtain the imaging signal output from the imaging unit 73 through the third signal cable 12 and the like. The display controller 61 applies predetermined processing to the obtained imaging signal. The display controller 61 controls the operation of the display device 4 through the first signal cable 10 and allows the display device 4 to display the image captured by the imaging unit 73. The display controller 61 causes the display device 4 to display an image corresponding to the shape of the flexible tube portion 72 estimated by the state quantity calculating unit 63.

The AC signal output unit 62 sequentially applies the alternating-current signal to each source coil 722 through the third signal cable 12 and the like.

The state quantity calculating unit 63 estimates the shape (a three-dimensional shape) of the flexible tube portion 72 (the insertion unit 7) based on the detection signal from the antenna 5. The state quantity calculating unit 63 calculates a bending angle θ of each of target segments 721 (a state quantity indicating a state of each of the segments 721) forming the flexible tube portion 72 based on the estimated shape of the flexible tube portion 72. A state change amount indicating a change amount from a reference state may also be used as the state quantity.

The origin specifying unit 64 specifies the segment 721 serving as an origin (hereinafter, referred to as an origin segment 721) to set a segment range indicating which segment the bending rigidity is to be changed or to set the bending rigidity, among a plurality of segments 721, based on the bending angle θ of each of the segments 721 calculated by the state quantity calculating unit 63.

The index value calculating unit 65 calculates the index value for changing the bending rigidity of each of a predetermined number of target segments 721 based on the bending angle θ of each of a predetermined number of target segments 721 set by the operation controller 66.

The operation controller 66 sets a predetermined number of (two or more) segments 721 continuously provided from the origin segment 721 toward a proximal end side of the flexible tube portion 72 out of all the segments 721 as the segments 721 (the target segments 721) whose bending rigidities are to be changed. As the target segments 721, it is also possible to set not a predetermined number of segments 721 continuously provided from the origin segment 721 toward the proximal end side of the flexible tube portion 72 but a predetermined number of segments 721 continuously provided from a reference segment 721 toward the proximal end side out of the segments 721 continuously provided from the origin segment 721 toward the proximal end side, the reference segment being the segment 721 adjacent to the origin segment 721 or one segment 721 away from the origin segment 721 by a predetermined number of segments 721.

The operation controller 66 applies the voltage at an initial voltage value (corresponding to an index value "0" in FIG. 3B) to each variable stiffness element 723 and sets the bending rigidity of the flexible tube portion 72 to that corresponding to the initial voltage value. Furthermore, the operation controller 66 changes the voltage value applied to the variable stiffness element 723 embedded in each of a predetermined number of target segments 721 through the third signal cable 12 and the like based on each index value calculated by the index value calculating unit 65 to change the bending rigidity of each of the predetermined number of target segments 721.

Operation of Endoscope Device

Next, reference will be made to operation of the above-described endoscope device 1 (a method for operating the endoscope device 1).

Figure 5:
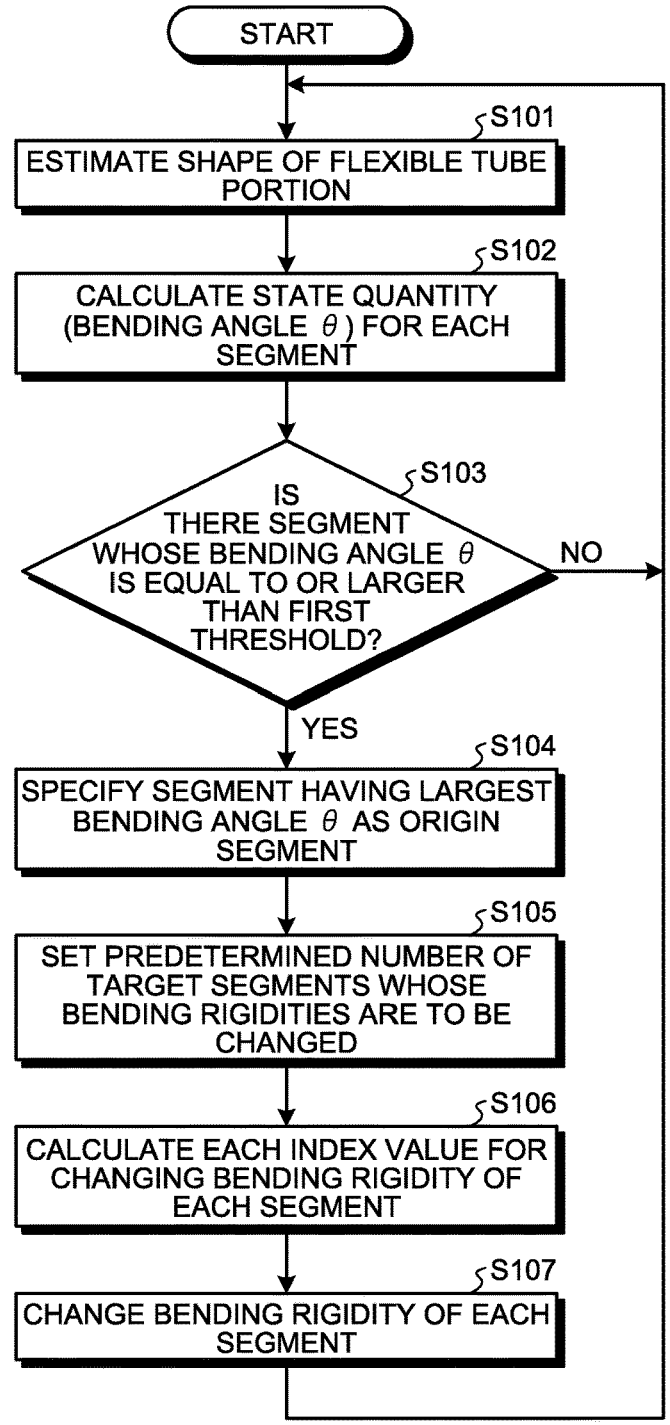
FIG. 5 is a flowchart illustrating operation of the endoscope device illustrated in FIG. 1.

FIG. 5 is a flowchart illustrating the operation of the endoscope device 1.

Hereinafter, the alternating-current signal is sequentially applied from the control device 6 (the AC signal output unit 62) to each source coil 722, the magnetic field generated by the source coil 722 is detected by the antenna 5, and the detection signal is output from the antenna 5 to the control device 6. The voltage at the initial voltage value is applied from the control device 6 (the operation controller 66) to each variable stiffness element 723 and the bending rigidity of the flexible tube portion 72 is set to that corresponding to the initial voltage value.

The state quantity calculating unit 63 inputs the detection signal from the antenna 5 and calculates a current position (three-dimensional position) of the target source coil 722 based on amplitude and a phase amount of the detection signal. The state quantity calculating unit 63 interpolates an interval between the calculated positions of the source coils 722 to estimate a current shape (three-dimensional shape) of the flexible tube portion 72 (step S101).

Subsequently, the state quantity calculating unit 63 calculates a current bending angle θ for each of the target segments 721 forming the flexible tube portion 72 as described later based on the shape of the flexible tube portion 72 estimated at step S101 (step S102: state quantity calculating step).

Figure 6:
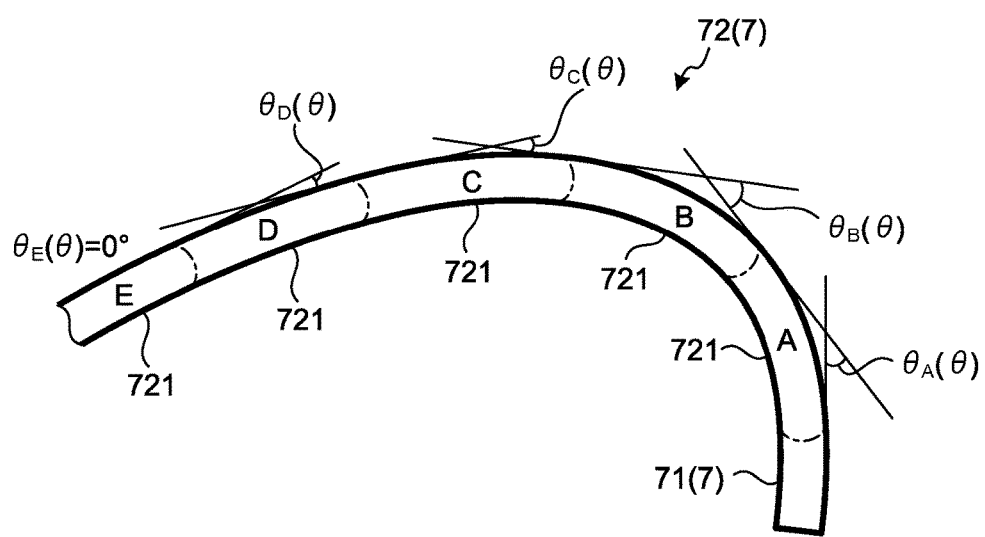
FIG. 6 is a schematic view of an insertion unit for explaining a method for calculating a bending angle illustrated in FIG. 5.

FIG. 6 is a schematic view illustrating a method for calculating the bending angle θ. Specifically, FIG. 6 illustrates an example of the shape of the flexible tube portion 72 estimated at step S101.

Only five segments 721 on a distal end side of an entire estimated shape of the flexible tube portion 72 are illustrated in FIG. 6 (there are a total of six or more segments 721 in the flexible tube portion 72). Hereinafter, the five segments 721 are referred to as first to fifth segments A to E in order from the distal end side. The bending angles θ of the first to fifth segments A to E are referred to as bending angles $\theta_A$ to $\theta_E$, respectively.

In order to calculate the bending angle $\theta_A$ of the first segment A, the state quantity calculating unit 63 focuses on linear elements corresponding to the first segment A among the entire shape of the flexible tube portion 72 estimated at step S101. The state quantity calculating unit 63 calculates, as the bending angle $\theta_A$, an angle between a tangent at a proximal end point of the first segment A (i.e., at a boundary between the second segment B and the first segment A, indicated by a dashed-dotted line in FIG. 6) and a tangent at a distal end point of the first segment A (i.e., at a boundary between the distal end portion 71 and the first segment A, indicated by a dashed-dotted line in FIG. 6) among the focused linear elements. The state quantity calculating unit 63 also calculates the bending angle θ of another segment 721 by the method similar to the method for calculating the bending angle $\theta_A$ of the first segment A described above.

In the example shown in FIG. 6, the bending angles $\theta_A$ to $\theta_E$ are calculated to be "4°", "3°", "3°", "2°", and "0°", respectively.

Subsequently, the origin specifying unit 64 determines whether there is the segment 721 whose bending angle θ is equal to or larger than a first threshold set in advance with reference to the bending angles θ of the target segments 721 calculated at step S102 (step S103).

If there is no segment 721 whose bending angle θ is equal to or larger than the first threshold (step S103: No), the endoscope device 1 returns to step S101. Then, the endoscope device 1 estimates the shape of the flexible tube portion 72 again.

On the other hand, if there is the segment 721 whose bending angle θ is equal to or larger than the first threshold (step S103: Yes), the origin specifying unit 64 specifies the segment 721 having the largest bending angle θ (in the example in FIG. 6, the first segment A having the largest bending angle θ) out of the target segments 721 calculated at step S102 as the origin segment 721 (step S104: origin specifying step). The segment 721 having the largest bending angle θ or the segment in the vicinity of the same is predicted to be in a stuck state (a state in which propulsion in a distal end direction is lost).

Subsequently, the operation controller 66 sets a predetermined number of (five, in the first embodiment) target segments 721 (the first to fifth segments A to E in the example in FIG. 6) continuously provided from the origin segment 721 toward the proximal end side (step S105).

Subsequently, the index value calculating unit 65 calculates the index value for changing the bending rigidity of each of a predetermined number of target segments 721 as described as follows based on the bending angle θ of each of a predetermined number of target segments 721 (step S106).

Specifically, when the index value calculating unit 65 calculates each index value, this adds the bending angle θ of one target segment 721 to the bending angle θ of the target segment 721 on the distal end side adjacent to the one target segment 721 out of a predetermined number of target segments 721 to calculate the index value for changing the bending rigidity of the one target segment 721.

Here, the index value corresponds to the voltage value of the voltage applied to the variable stiffness element 723 embedded in each target segment 721, and when the index value is "0", the voltage value is the highest (the initial voltage value) as illustrated in FIG. 3B. That is to say, when the voltage at the initial voltage value corresponding to the index value "0" is applied to the variable stiffness element 723, the bending rigidity of the variable stiffness element 723 (the segment 721) is the highest (the stiffness of the segment 721 is the highest). As the index value increases, the voltage value of the voltage applied to the variable stiffness element 723 decreases. That is to say, as the index value increases, the voltage applied to the variable stiffness element 723 decreases and the bending rigidity of the variable stiffness element 723 (the segment 721) decreases (the stiffness of the segment 721 decreases). In FIG. 3B, when the index value is "10" or larger, the voltage value of the voltage applied to the variable stiffness element 723 is set to "0".

In the example in FIG. 6, the index value calculating unit 65 calculates each index value as shown in the following Table 1.

TABLE 1

| | Target Segment | | | | |
|---|---|---|---|---|---|
| | First Segment A | Second Segment B | Third Segment C | Fourth Segment D | Fifth Segment E |
| 1: Bending Angle θ (deg.) | 4 | 3 | 3 | 2 | 0 |
| 2: Bending Angle θ of Adjacent Target Segment on Distal End Side (deg.) | 0 | 4 | 3 | 3 | 2 |
| Index Value (1 + 2) | 4 | 7 | 6 | 5 | 2 |

That is, when the index value calculating unit 65 calculates the index value for changing the bending rigidity of the first segment A, for example, this adds the bending angle θ of the target segment 721 on the distal end side adjacent to the first segment A (since the distal end side is the distal end portion 71, the bending angle θ=0) to the bending angle $\theta_A$ (4) of the first segment A to calculate the index value to be "4" as illustrated in Table 1. By the similar method, the index value calculating unit 65 calculates the index values for changing the bending rigidity of the second segment B to the fifth segment E to be "7", "6", "5", and "2", respectively.

Subsequently, the operation controller 66 applies the voltage at each voltage value corresponding to each index value calculated at step S106 to the variable stiffness element 723 embedded in each of a predetermined number of target segments 721 (the first to fifth segments A to E in the example in FIG. 6) through the third signal cable 12 and the like to change the bending rigidity of each of the predetermined number of target segments 721 (step S107: operation controlling step). Thereafter, the endoscope device 1 returns to step S101. Then, the endoscope device 1 estimates the current shape of the flexible tube portion 72 again.

In the example in FIG. 6, the voltages corresponding to the index values "4", "7", "6", "5", and "2" are applied to the variable stiffness elements 723 embedded in the first to fifth segments A to E, respectively. Therefore, the bending rigidity (stiffness) of the second segment B on the proximal end side adjacent to the first segment A being the origin segment is the lowest. That is to say, the bending rigidity (stiffness) of the segment 721 on the proximal end side adjacent to the segment 721 having the largest bending angle θ (state quantity) is the lowest in the above-described example (FIG. 6 and Table 1). Although the bending rigidity of the segment 721 on the proximal end side adjacent to the segment 721 having the largest bending angle θ is the lowest in the above-described example, depending on the value of the bending angle θ of each segment 721 (for example, when the bending angle θ of the second segment B is not "3" but "5" in Table 1), the bending rigidity of the segment 721 having the largest bending angle θ (the second segment B in this case) is the lowest. That is to say, in the first embodiment, the bending rigidity of the segment 721 having the largest bending angle θ is the lowest, or the bending rigidity of the segment 721 on the proximal end side adjacent to the segment 721 having the largest bending angle θ is the lowest.

Reference will be made below to an effect of a case in which the bending rigidity of the segment 721 on the proximal end side of the segment 721 having the largest state quantity is decreased.

Figure 7A:
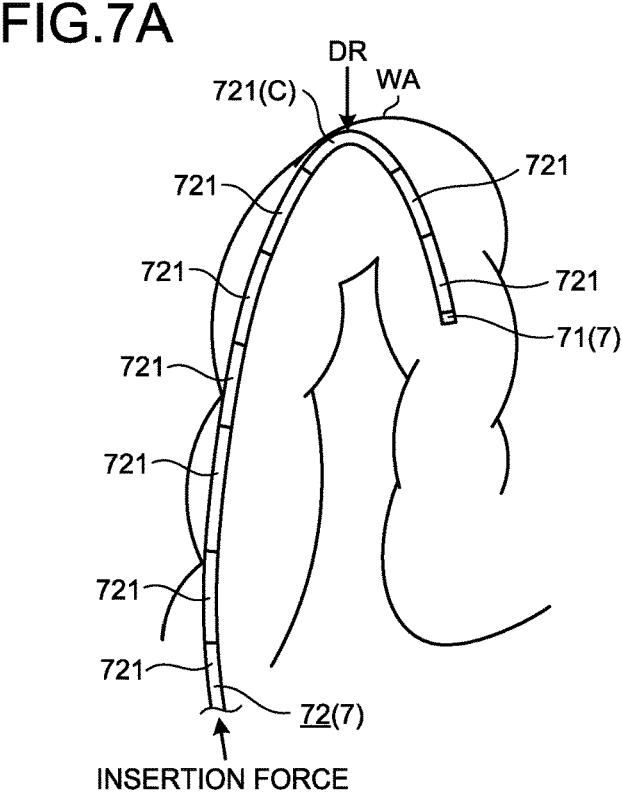
FIG. 7A is a schematic view illustrating an effect when decreasing bending rigidity (stiffness) of a segment on a proximal end side of the segment having a largest state quantity.
Figure 7B:
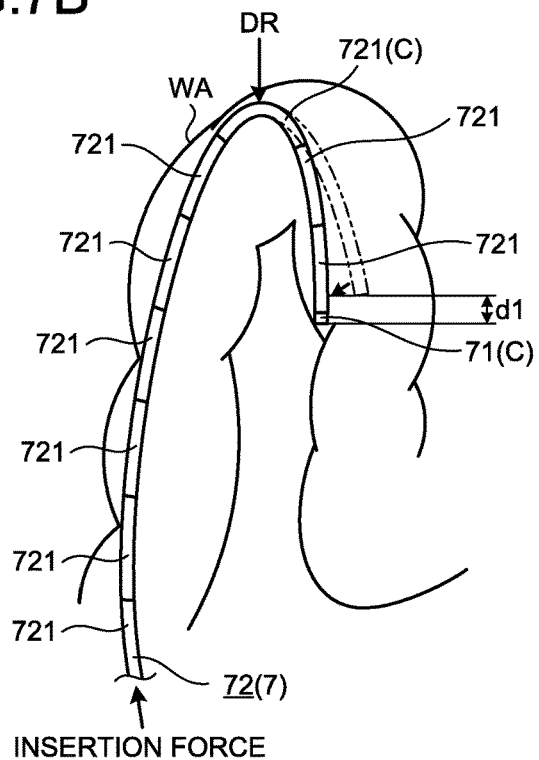
FIG. 7B is a schematic view illustrating the effect when decreasing the bending rigidity (stiffness) of the segment on the proximal end side of the segment having the largest state quantity.
Figure 7C:
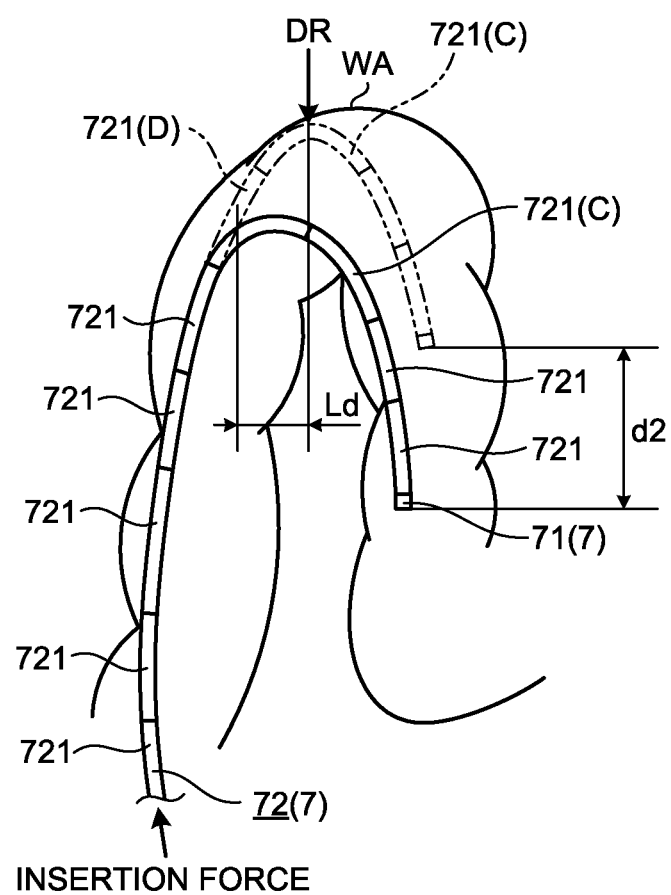
FIG. 7C is a schematic view illustrating the effect when decreasing the bending rigidity (stiffness) of the segment on the proximal end side of the segment having the largest state quantity.

FIGS. 7A to 7C are schematic views for illustrating the above-described effect. Specifically, FIGS. 7A and 7B sequentially illustrate a state of the insertion unit 7 in a case in which the operator applies insertion force in the distal end direction to the insertion unit 7 inserted into the large intestine, the case in which only the bending rigidity (stiffness) of the segment 721 having the largest state quantity is decreased. FIG. 7C illustrates the state of the insertion unit 7 in a case in which the operator applies the insertion force in the distal end direction to the insertion unit 7 inserted into the large intestine from the state illustrated in FIG. 7A, the case in which only the bending rigidity (stiffness) of the segment 721 on the proximal end side adjacent to the segment 721 having the largest state quantity is decreased.

Here, "DR" shown in FIGS. 7A to 7C represents drag force applied from a body cavity wall WA to the insertion unit 7 when the operator applies the insertion force to the insertion unit 7 inserted into the living body from the proximal end side toward the distal end side.

As illustrated in FIG. 7A, suppose that the insertion unit 7 is inserted into the large intestine and the third segment C (the segment 721 widely bent in FIG. 7A) of the insertion unit 7 abuts on the body cavity wall WA of a bent portion in the large intestine.

In this case, the third segment C becomes the segment 721 having the largest state quantity (bending angle θ). When only the bending rigidity of the third segment C is decreased, the insertion unit 7 is configured such that a bending amount of the third segment C increases according to the amount of the insertion force applied by the operator to the insertion unit 7 (the drag force DR), and as a result, a distal end portion advances in the distal end direction (vertical direction) by length d1 as illustrated in FIG. 7B.

On the other hand, when only the bending rigidity of the fourth segment D on the proximal end side adjacent to the third segment C is decreased, bending moment applied to the fourth segment D is obtained by multiplying distance Ld (distance in a horizontal direction between a central position of the third segment C and a central position of the fourth segment D) by the drag force DR; the moment is larger than the bending moment of the third segment C illustrated in FIG. 7B. Therefore, the distal end portion of the insertion unit 7 advances in the distal end direction by length d2 longer than the length d1 according to the insertion force applied by the operator to the insertion unit 7 (the drag force DR) as illustrated in FIG. 7C.

That is, by decreasing the bending rigidity of the segment 721 on the proximal end side adjacent to the segment 721 having the largest state quantity, the distal end of the insertion unit 7 may further advance in the distal end direction as compared to a case in which the bending rigidity of the segment 721 having the largest state quantity is decreased.

In the first embodiment, as the state quantity of each of a plurality of segments 721 is larger, the bending rigidity of the segment 721 on the proximal end side adjacent to one segment tends to decrease. The state quantity itself can be used as an index value, for example, such that as the state quantity of each of the plurality of segments 721 is larger, the bending rigidity of the segment 721 decreases. A different configuration may be employed such that as the state quantity of each of the plurality of segments 721 is larger, the bending rigidity of a segment away from one segment 721 by a predetermined number of segments decreases. An alternative configuration may also be employed such that the index value based on the state quantity (including a case in which the state quantity itself is used as the index value) is compared with a predetermined threshold and when the index value of one segment is larger than the threshold, the bending rigidity of the one segment, the bending rigidity of a segment 721 adjacent to the one segment, or the bending rigidity of a segment 721 away from the one segment by a predetermined number of segments decreases (set to be predetermined lower bending rigidity).

According to the first embodiment described above, the following effects can be obtained.

Figure 8A:
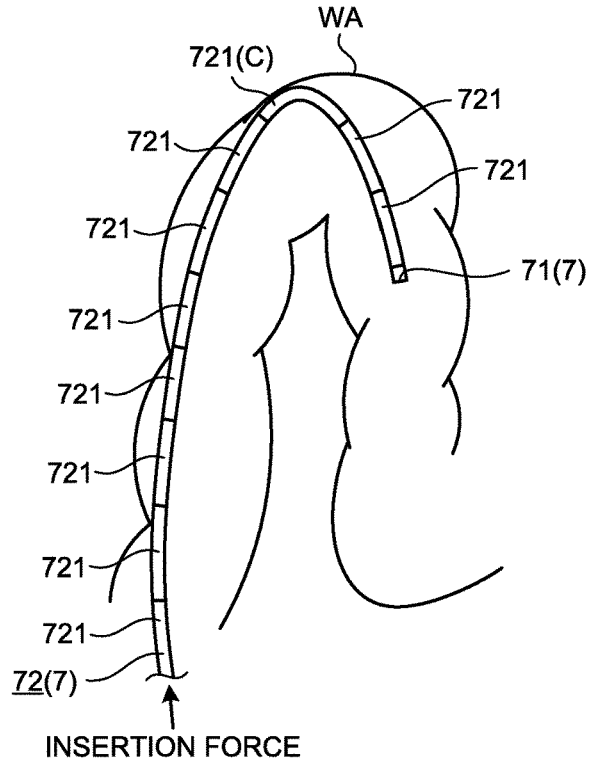
FIG. 8A is a schematic view for illustrating an effect of the first embodiment of the present invention.
Figure 8B:
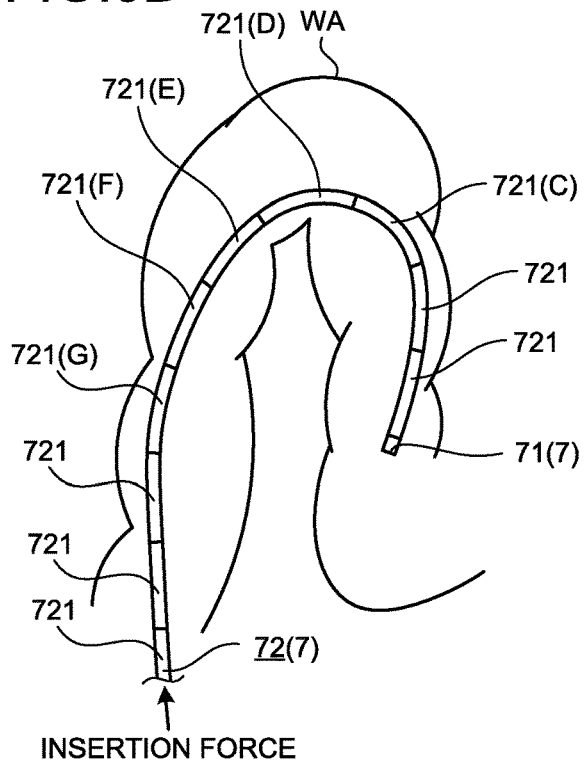
FIG. 8B is a schematic view for illustrating the effect of the first embodiment of the present invention.

FIGS. 8A and 8B are schematic views for illustrating the effect of the first embodiment of the present invention. Specifically, FIGS. 8A and 8B sequentially illustrate the state of the insertion unit 7 when the operator applies the insertion force to the insertion unit 7 inserted into the large intestine in the distal end direction.

As illustrated in FIG. 8A, suppose that the insertion unit 7 is inserted into the large intestine and the third segment C (the segment 721 widely bent in FIG. 8A) of the insertion unit 7 abuts on the body cavity wall WA of the bent portion in the large intestine.

In this case, the endoscope device 1 decreases the bending rigidity of the third segment C being the origin segment and the fourth to seventh segments D to G continuously provided on the proximal end side of the third segment C. As a result, when the operator applies the insertion force to the insertion unit 7, bending amounts of the third to seventh segments C to G increase and an entire insertion unit 7 has an obtuse-angled shape as illustrated in FIG. 8B. That is to say, the insertion unit 7 is brought into contact with the body cavity wall WA in the obtuse-angled shape and pressure applied from the body cavity wall WA decreases. Therefore, when the insertion force is applied to the insertion unit 7, the insertion force is not converted to force to extend the large intestine (force pushing the body cavity wall WA) but is effectively utilized as the force to advance the distal end of the insertion unit 7 and it is possible to facilitate passage through the bent portion of the large intestine.

According to the endoscope device 1 of the first embodiment, it is possible to facilitate the insertion into the lumen easier and to improve operability.

Especially, when the endoscope device 1 according to the first embodiment changes the bending rigidity of the third to seventh segments C to G being the target segments, this decreases the bending rigidity of one target segment 721 as the index value is larger according to the index value obtained by adding the bending angle θ of the one target segment 721 to the bending angle θ of the target segment 721 on the distal end side adjacent to the one target segment 721 out of the target segments.

Therefore, the fourth segment D and the subsequent segments on the proximal end side of the third segment C subjected to the drag force from the bent portion of the large intestine are easily bent and further the bending rigidity is continuous in the third to seventh segments C to G, so that pain of a subject due to a load on the bent portion of the large intestine may be effectively decreased.

The endoscope device 1 according to the first embodiment does not change the bending rigidities of all the target segments 721 but changes the bending rigidities of the third to seventh segments C to G located around the bent portion of the large intestine in the above-described case (FIG. 8A).

Therefore, it is not required to calculate the index values of all the segments 721 and a processing load of the control device 6 can be decreased.

The endoscope device 1 according to the first embodiment specifies the third segment C having the largest bending angle θ out of the target segments 721 as the origin segment.

Therefore, it is possible to accurately specify the segment 721 predicted to be in the stuck state (the state in which the propulsion in the distal end direction is lost), specify the third to seventh segments C to G appropriate as the target segments whose bending rigidities are to be changed using the segment 721 in the stuck state as the origin, and specify the fourth segment D whose bending rigidity is changed the most. With this feature, it is possible to appropriately change the bending rigidity of the target segment 721 to facilitate the passage through the bent portion of the large intestine.

The endoscope device 1 according to the first embodiment uses a plurality of source coils 722 and the antenna 5 to calculate the bending angle θ of each of the target segments 721 based on the detection signal from the antenna 5. The endoscope device 1 starts changing the bending rigidity of the target segment 721 if there is the segment 721 whose bending angle θ is equal to or larger than the first threshold set in advance.

Therefore, it is considered that the bending angle θ of the origin segment 721 predicted to be in the stuck state becomes larger according to the drag force from the body cavity wall of the large intestine, so that it is possible to successfully predict the stuck state to avoid the stuck state by calculating the bending angle θ of each of the target segments 721.

The target segments 721 whose bending angles are to be calculated may be all the segments forming the flexible tube portion 72 or part of the segments.

Second Embodiment

Next, a second embodiment of the present invention will be described.

The same reference signs are used to designate the same elements and the same steps as those of the above-described first embodiment, and detailed explanation thereof will be omitted or simplified.

An endoscope device according to the second embodiment is different from the endoscope device 1 described in the above-described first embodiment in a method for specifying an origin segment. The endoscope device according to the second embodiment is obtained by changing some functions of the control device 6 of the endoscope device 1 described in the above-described first embodiment.

Configuration of Control Device

Reference will be made below to a configuration of a control device in the endoscope device according to the second embodiment.

Figure 9:
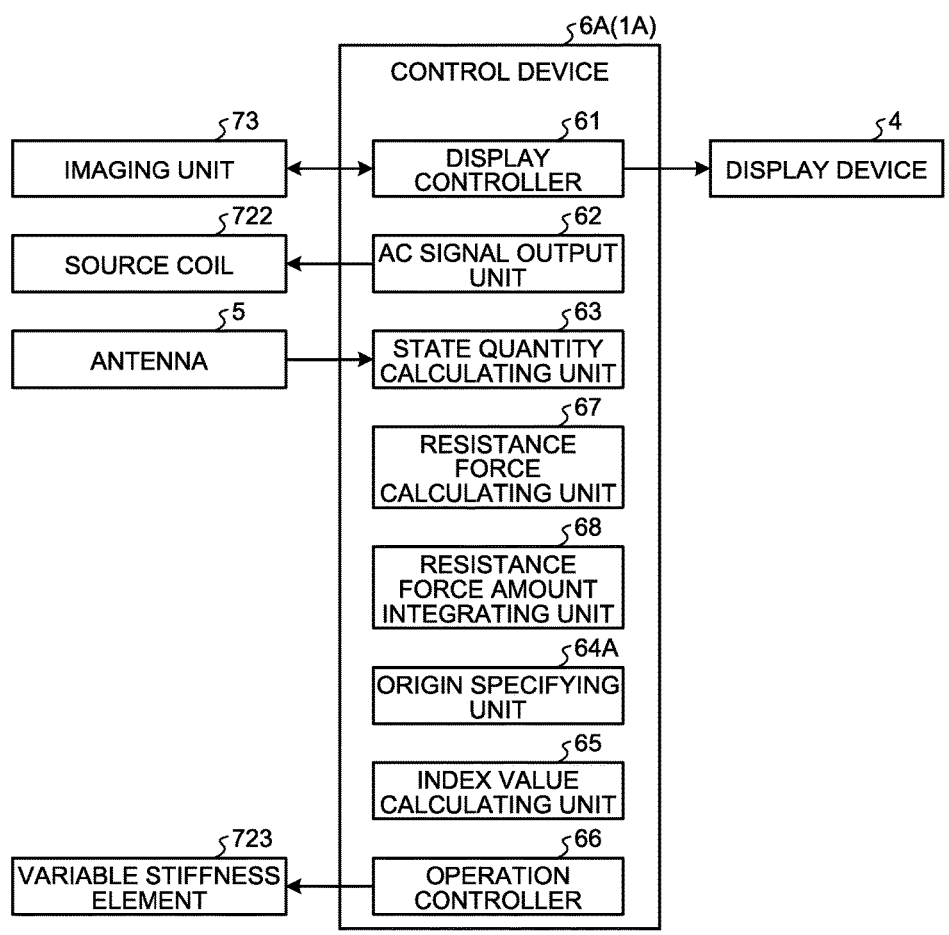
FIG. 9 is a block diagram illustrating a configuration of a control device in an endoscope device according to a second embodiment of the present invention.

FIG. 9 is a block diagram illustrating a configuration of a control device 6A in an endoscope device 1A according to the second embodiment of the present invention.

The control device 6A is configured by adding a resistance force calculating unit 67 and a resistance force amount integrating unit 68 and by adding an origin specifying unit 64A obtained by changing some functions of the origin specifying unit 64 in place of the origin specifying unit 64 to the control device 6 (FIG. 4) described in the above-described first embodiment as illustrated in FIG. 9.

The resistance force calculating unit 67 calculates resistance force by friction of each of all segments 721 forming a flexible tube portion 72 based on a bending angle θ of each segment 721 calculated by the state quantity calculating unit 63.

The resistance force amount integrating unit 68 integrates the amounts of the resistance force calculated by the resistance force calculating unit 67 in order from the segment 721 on a most proximal end side out of all the segments 721.

Each time the amount of the resistance force of one segment 721 is integrated by the resistance force amount integrating unit 68, the origin specifying unit 64A compares an integrated value which is integrated with a second threshold set in advance. When the integrated value becomes equal to or larger than the second threshold, the origin specifying unit 64A specifies the segment 721 having the amount of the resistance force integrated last by the resistance force amount integrating unit 68, as the origin segment 721.

Operation of Endoscope Device

Next, reference will be made to operation of the endoscope device 1A (a method for operating the endoscope device 1A) according to the second embodiment.

FIG. 10 is a flowchart illustrating the operation of the endoscope device 1A.

The operation of the endoscope device 1A according to the second embodiment is different from the operation of the endoscope device 1 (FIG. 5) described in the above-described first embodiment only in that steps S108 to S111 are added and step S104A is added in place of step S104 as illustrated in FIG. 10. Therefore, only steps S108 to S111 and S104A are hereinafter described.

Figure 11A:
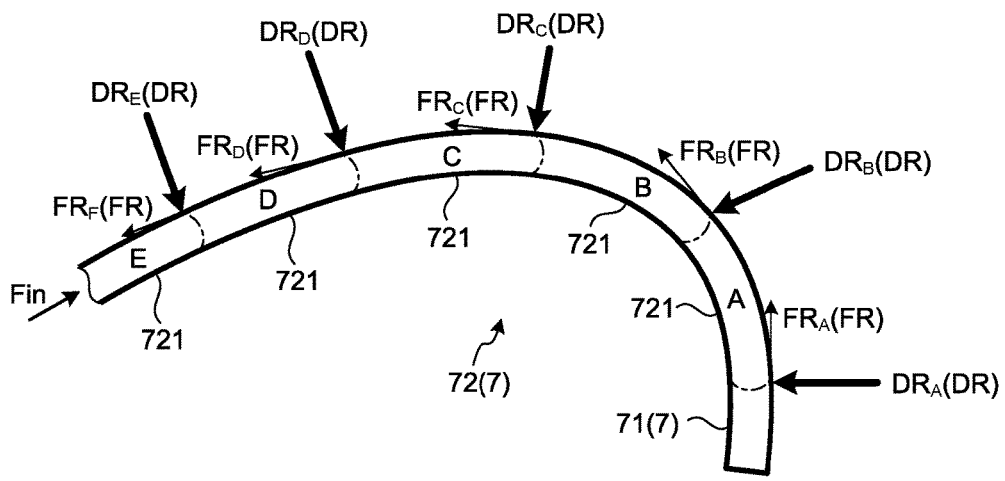
FIG. 11A is a schematic view of the insertion unit for explaining a calculation of resistance force for each segment illustrated in FIG. 10.
Figure 11B:
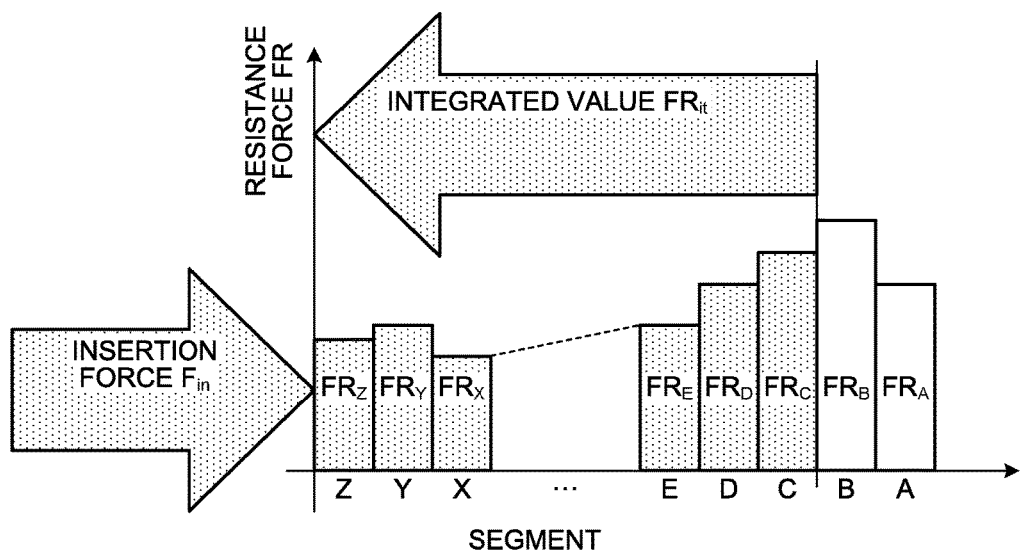
FIG. 11B is a schematic view for explaining an integral of amounts of resistance force illustrated in FIG. 10.

FIGS. 11A and 11B are schematic views for illustrating steps S108 and S109. Specifically, FIG. 11A corresponds to FIG. 6.

In FIGS. 11A and 11B, the flexible tube portion 72 has a total of 26 segments 721. Hereinafter, the 26 segments 721 are referred to as first to 26th segments A to Z in order from a distal end side. Bending angles θ of the first to 26th segments A to Z are referred to as bending angles $\theta_A$ to $\theta_Z$, respectively.

Here, "DR" shown in FIG. 11A represents drag force applied from a body cavity wall to each segment 721 when an operator applies insertion force $F_{in}$ (FIG. 11B) from the proximal end side toward the distal end side to an insertion unit 7 inserted into a living body, as in FIGS. 7A to 7C. Hereinafter, the drag forces DR applied to the first to 26th segments A to Z are represented as drag forces $DR_A$ to $DR_Z$, respectively.

"FR" shown in FIGS. 11A and 11B represents the resistance force by the friction with the body cavity wall of each segment 721 in the above-described case. Hereinafter, amounts of the resistance force of the first to 26th segments A to Z are represented as resistance force $FR_A$ to $FR_Z$, respectively.

Step S108 is executed after step S102.

Specifically, the resistance force calculating unit 67 calculates a current resistance force of each of all the segments 721 forming the flexible tube portion 72 as described later at step S108.

First, the resistance force calculating unit 67 calculates current drag force DR applied to each of all the segments 721 by following equation (1).

$$DR = k \cdot \theta \quad (1)$$

In equation (1), k representing a bending elasticity coefficient (N/deg.) of a corresponding segment 721 is obtained from current bending rigidity of the segment 721 (corresponding to a current voltage value applied to the segment 721 (FIG. 3B)).

In an example in FIGS. 11A and 11B, the resistance force calculating unit 67 calculates the current drag forces DR ($DR_A$ to $DR_Z$) applied to the first to 26th segments A to Z, respectively, by equation (1) by using current bending angles θ ($\theta_A$ to $\theta_Z$) and current bending elasticity coefficients k ($k_A$ to $k_Z$) of the first to 26th segments A to Z, respectively.

Then, the resistance force calculating unit 67 calculates the current resistance force FR of each of all the segments 721 by following equation (2) by using the current drag forces DR applied to all the calculated segments 721 and a dynamic friction coefficient μ (the same for all the segments 721) on a surface of the flexible tube portion 72.

$$FR = \mu \cdot DR$$
$$= \mu \cdot k \cdot \theta \quad (2)$$

In the example in FIGS. 11A and 11B, the resistance force calculating unit 67 substitutes the current drag forces DR ($DR_A$ to $DR_Z$) of the first to 26th segments A to Z, respectively, into a right side of equation (2) to calculate the amounts of the current resistance force FR ($FR_A$ to $FR_Z$) of the first to 26th segments A to Z, respectively.

Step S109 is executed after step S108.

Specifically, the resistance force amount integrating unit 68 integrates the amounts of the resistance force FR calculated at step S108 in order from the segment 721 on the most proximal end side (the 26th segment Z in the example in FIGS. 11A and 11B) among all the segments 721 at step S109.

Step S110 is executed after step S109.

Specifically, each time the amount of the resistance force FR of one segment 721 is integrated at step S109, the origin specifying unit 64A compares an integrated value $FR_{it}$ which is integrated (FIG. 11B) with the second threshold set in advance at step S110. Then, the origin specifying unit 64A determines whether the integrated value becomes equal to or larger than the second threshold.

A case in which the integrated value $FR_{it}$ ($FR_Z+FR_Y+FR_X+ \ldots +FR_C$) is equal to or larger than the second threshold when the amounts of the resistance force FR of the 26th segment Z to the third segment C are integrated is illustrated in FIG. 11B.

Step S111 is executed when the integrated value is determined to be smaller than the second threshold at step S110 (step S110: No (in the example in FIG. 11B, when the amounts of the resistance force FR of the 26th segment Z to the third segment C are not integrated)).

Specifically, the origin specifying unit 64A determines whether the amounts of the resistance force FR of all the segments 721 (the first to 26th segments A to Z in the example in FIGS. 11A and 11B) are integrated at step S111.

When the amounts of the resistance force FR of all the segments 721 are not integrated (step S111: No), the endoscope device 1A returns to step S109. Then, the endoscope device 1A further integrates the amount of the resistance force FR of the segment 721 on the distal end side adjacent to the segment 721, the amount of the resistance force FR is most recently integrated.

On the other hand, if the amounts of the resistance force FR of all the segments 721 are integrated (step S111: Yes), that is, when the integrated value is smaller than the second threshold even when the amounts of the resistance force FR of all the segments 721 are integrated, the endoscope device 1A returns to step S101. Then, the endoscope device 1A estimates a shape of the flexible tube portion 72 again.

Step S104A (origin specifying step) is executed when the integrated value is determined to be equal to or larger than the second threshold at step S110 (step S110: Yes (in the example in FIG. 11B, when the amounts of the resistance force FR of the 26th segment Z to the third segment C are integrated)).

Specifically, the origin specifying unit 64A specifies the segment 721 having the amount of the resistance force FR integrated last at step S109 (the third segment C in the example in FIG. 11B) as the origin segment 721. Thereafter, the endoscope device 1A proceeds to step S105. Then, the endoscope device 1A specifies a predetermined number of target segments 721 (the third to seventh segments C to G in the example in FIG. 11B) as in the above-described first embodiment.

According to the second embodiment described above, the following effects can be obtained in addition to the effect similar to that of the above-described first embodiment.

The endoscope device 1A according to the second embodiment integrates the amounts of the resistance force FR in order from the segment 721 on the most proximal end side out of all the segments 721. When the integrated value becomes equal to or larger than the second threshold, the endoscope device 1A specifies the segment 721 having the amount of the resistance force FR integrated last, as the origin segment.

Therefore, since a stuck state is considered to occur when the integrated value of the amounts of the resistance force FR becomes larger than a predetermined threshold, it is possible to appropriately specify the segment 721 predicted to be in the stuck state based on a comparison result of the integrated value of the amounts of the resistance force FR with the second threshold, further specify a range of the segments 721 indicating which segment the bending rigidity is to be changed, based on a specification result, and change the bending rigidity of a plurality of segments 721 within the range, thereby successfully avoiding the stuck state.

Third Embodiment

Next, a third embodiment of the present invention will be described.

The same reference signs are used to designate the same elements and the same steps as those of the above-described first and second embodiments, and detailed explanation thereof will be omitted or simplified.

An endoscope device according to the third embodiment is different from the endoscope devices 1 and 1A described in the above-described first and second embodiments, respectively, in a condition serving as a trigger to change bending rigidity of each segment 721. The endoscope device according to the third embodiment is obtained by changing some functions of the control devices 6 and 6A of the endoscope devices 1 and 1A described in the above-described first and second embodiments, respectively.

Configuration of Control Device

Reference will be made below to a configuration of a control device in the endoscope device according to the third embodiment.

Figure 12:
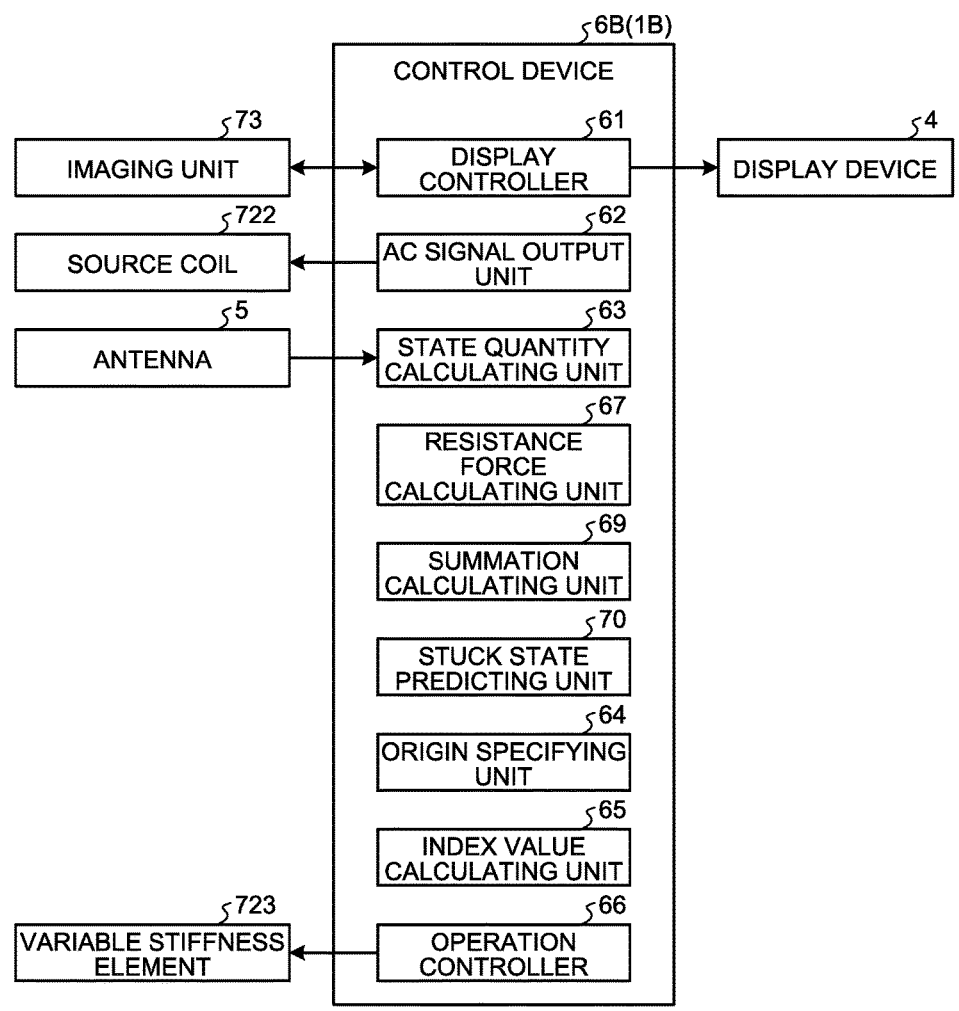
FIG. 12 is a block diagram illustrating a configuration of a control device in an endoscope device according to a third embodiment of the present invention.

FIG. 12 is a block diagram illustrating a configuration of a control device 6B in an endoscope device 1B according to the third embodiment of the present invention.

The control device 6B is configured by adding the resistance force calculating unit 67 described in the above-described second embodiment, a summation calculating unit 69, and a stuck state predicting unit 70 to the control device 6 (FIG. 4) described in the above-described first embodiment as illustrated in FIG. 12.

The summation calculating unit 69 calculates a sum of amounts of resistance force FR of all the segments 721 calculated by the resistance force calculating unit 67.

The stuck state predicting unit 70 compares the sum obtained by the summation calculating unit 69 with a third threshold set in advance and predicts whether an insertion unit 7 is put into a stuck state in which propulsion in a distal end direction is lost.

In the third embodiment, the endoscope device 1B changes bending rigidity of each segment 721 when predicting the stuck state.

Operation of Endoscope Device

Next, reference will be made to operation of the endoscope device 1B (a method for operating the endoscope device 1B) according to the third embodiment.

Figure 13:
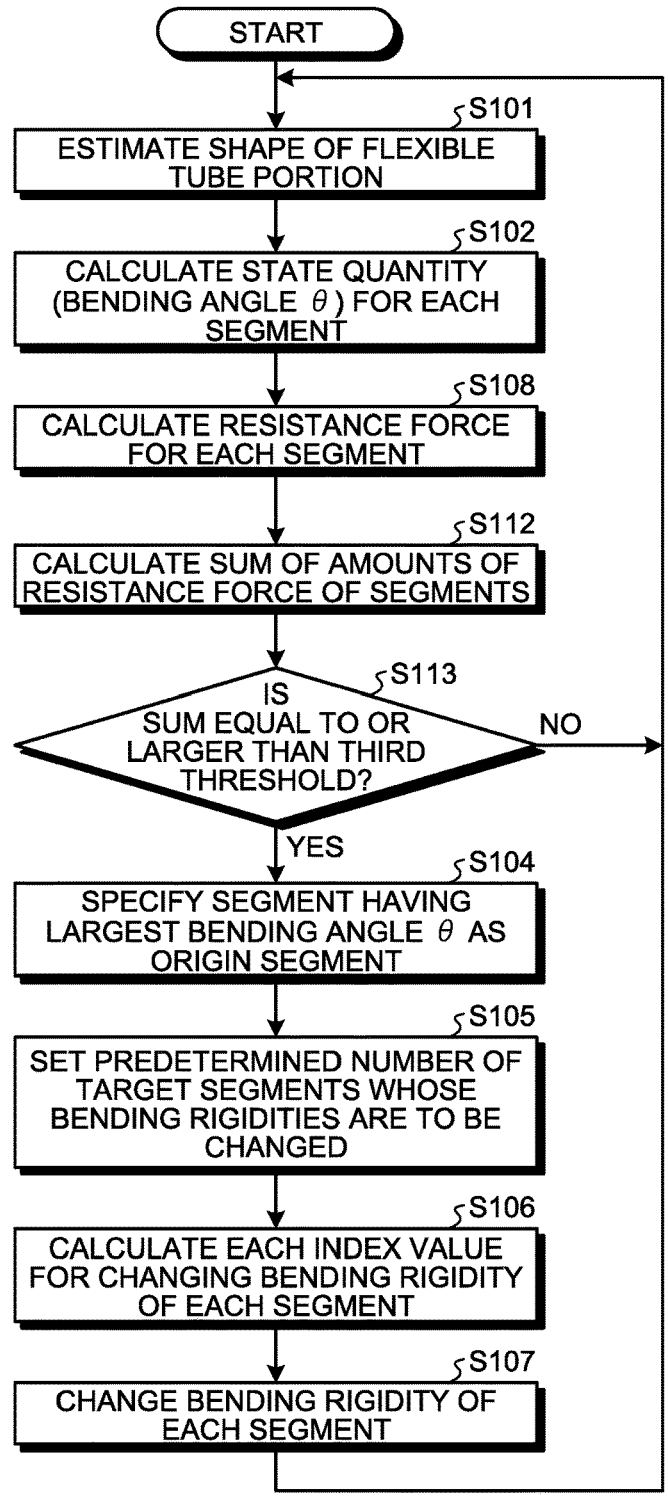
FIG. 13 is a flowchart illustrating operation of the endoscope device illustrated in FIG. 12.

FIG. 13 is a flowchart illustrating the operation of the endoscope device 1B.

The operation of the endoscope device 1B according to the third embodiment is different from the operation of the endoscope device 1 (FIG. 5) described in the above-described first embodiment only in that step S108 described in the above-described second embodiment is added and steps S112 and S113 are added as illustrated in FIG. 13. Therefore, only steps S112 and S113 will be hereinafter described.

Step S112 is executed after step S108.

Specifically, the summation calculating unit 69 calculates the sum of the amounts of the resistance force FR of all the segments 721 calculated at step S108 (in the example in FIGS. 11A and 11B, $FR_A+FR_B+FR_C+ \ldots +FR_Z$) at step S112.

Step S113 is executed after step S112.

Specifically, the stuck state predicting unit 70 compares the sum obtained at step S112 with the third threshold set in advance to determine whether the sum is equal to or larger than the third threshold at step S113.

When the sum is smaller than the third threshold (step S113: No), the stuck state predicting unit 70 predicts that the insertion unit 7 is not put into the stuck state for the meantime. Then, the endoscope device 1B returns to step S101 and estimates a shape of a flexible tube portion 72 again.

On the other hand, when the sum is equal to or larger than the third threshold (step S113: Yes), the stuck state predicting unit 70 predicts that the insertion unit 7 is put into the stuck state. Then, the endoscope device 1B proceeds to step S104 and sequentially executes steps S104 to S107, thereby changing the bending rigidity of a predetermined number of target segments 721.

Even if the bending rigidity of each segment 721 is changed when the stuck state is predicted as in the third embodiment described above, an effect similar to that in the above-described first and second embodiments can be obtained.

Fourth Embodiment

Next, a fourth embodiment of the present invention will be described.

The same reference signs are used to designate the same elements and the same steps as those of the above-described third embodiment, and detailed explanation thereof will be omitted or simplified.

An endoscope device according to the fourth embodiment is different from the endoscope device 1B described in the above-described third embodiment in that all segments 721 are set as target segments whose bending rigidities are to be changed. The endoscope device according to the fourth embodiment is obtained by changing some functions of the control device 6B of the endoscope device 1B described in the above-described third embodiment.

Configuration of Control Device

Reference will be made below to a configuration of a control device in the endoscope device according to the fourth embodiment.

Figure 14:
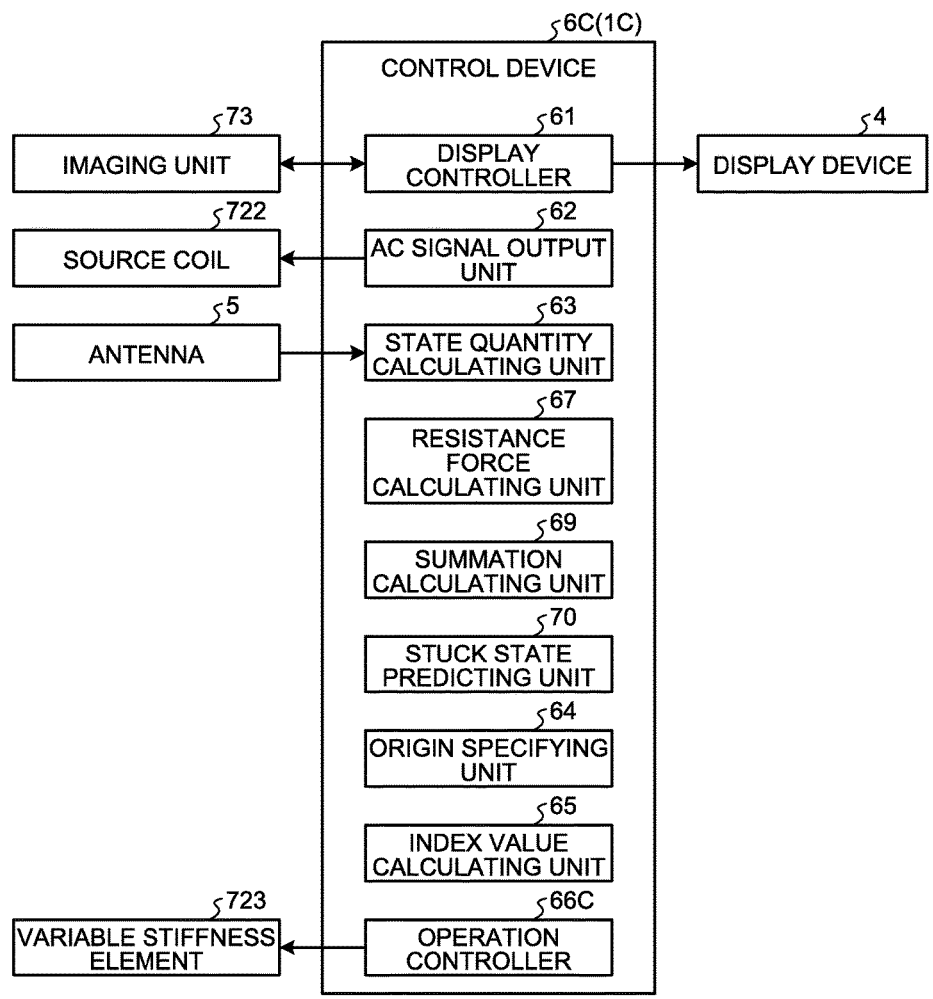
FIG. 14 is a block diagram illustrating a configuration of a control device in an endoscope device according to a fourth embodiment of the present invention.

FIG. 14 is a block diagram illustrating a configuration of a control device 6C in an endoscope device 1C according to the fourth embodiment of the present invention.

The control device 6C is configured such that an operation controller 66C obtained by changing some functions of the operation controller 66 is added in place of the operation controller 66 to the control device 6B (FIG. 12) described in the above-described third embodiment as illustrated in FIG. 14.

The operation controller 66C is different from the operation controller 66 described in the above-described third embodiment in that all the segments 721 are set to be the target segments 721 whose bending rigidity is changed.

Operation of Endoscope Device

Next, reference will be made to operation of the endoscope device 1C (a method for operating the endoscope device 1C) according to the fourth embodiment.

Figure 15:
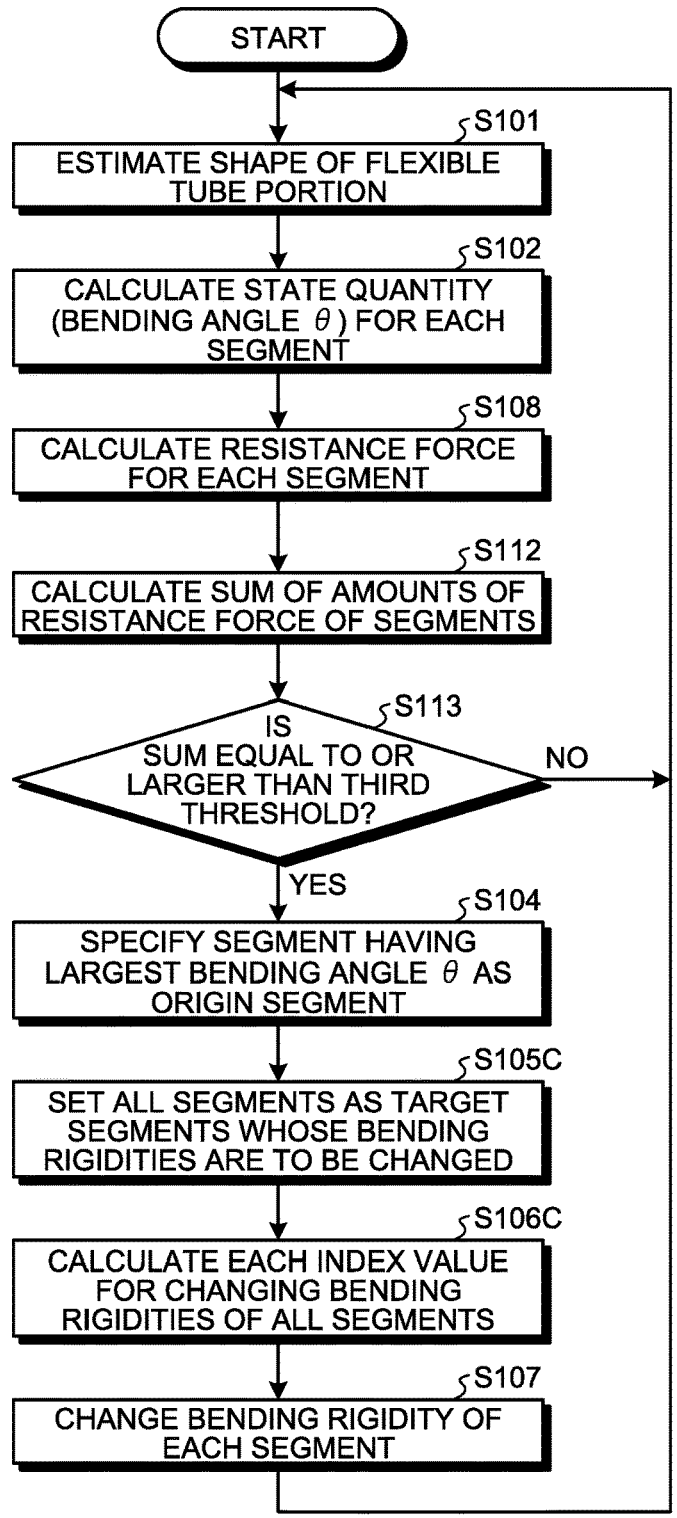
FIG. 15 is a flowchart illustrating operation of the endoscope device illustrated in FIG. 14.

FIG. 15 is a flowchart illustrating the operation of the endoscope device 1C.

The operation of the endoscope device 1C according to the fourth embodiment is different from the operation of the endoscope device 1B (FIG. 13) described in the above-described third embodiment only in that steps S105C and S106C are added in place of steps S105 and S106, respectively, as illustrated in FIG. 15. Therefore, only steps S105C and S106C will be hereinafter described.

Step S105C is executed after step S104.

Specifically, the operation controller 66C sets all the segments 721 (first to 26th segments A to Z in the example in FIGS. 11A and 11B) as the target segments 721 whose bending rigidities are to be changed, at step S105C.

Subsequently, an index value calculating unit 65 calculates an index value at which the bending rigidity of the origin segment 721 specified at step S104 or the segment 721 on a proximal end side adjacent to the origin segment 721 is the lowest by a method similar to that at step S106 described in the above-described third embodiment at step S106C. Alternatively, the index value calculating unit 65 calculates the index value at which the bending rigidity of the segment 721 away from the origin segment 721 by a predetermined number of segments 721 is the lowest. As for the index values for changing the bending rigidity of other segments 721, the index value calculating unit 65 calculates the index values such that the bending rigidity increases with distance from the segment 721 whose bending rigidity is set to be the lowest. Thereafter, the endoscope device 1C proceeds to step S107. Then, the endoscope device 1C changes the bending rigidity of all the segments 721.

Even if all the segments 721 are set as the target segments whose bending rigidities are to be changed as in the above-described fourth embodiment, an effect similar to that in the above-described third embodiment can be obtained.

Other Embodiments

Although the mode for carrying out the present invention is heretofore described, the present invention is not be limited only to the above-described first to fourth embodiments.

Figure 16:
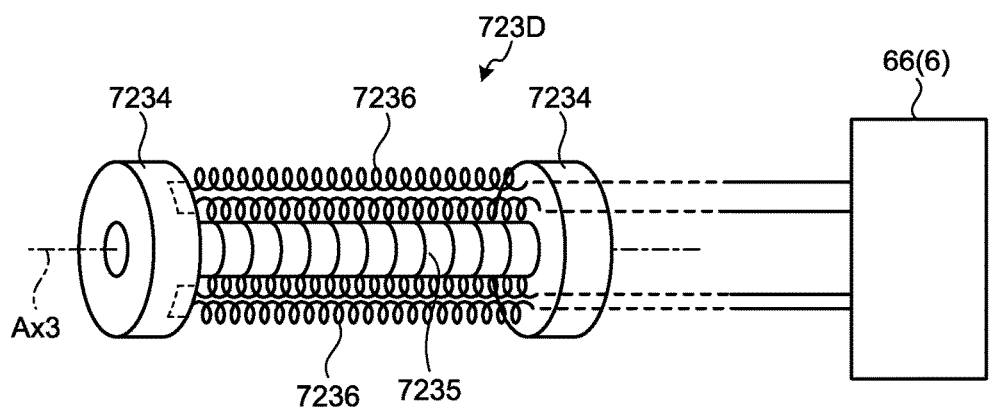
FIG. 16 is a schematic view illustrating a modification of the first to fourth embodiments of the present invention.

FIG. 16 is a schematic view illustrating a modification of the first to fourth embodiments.

Although the variable stiffness element 723 is adopted as the variable rigidity portion in the above-described first to fourth embodiments, it is also possible to adopt a shape memory alloy actuator 723D (hereinafter, referred to as a shape memory alloy (SMA) actuator 723D) illustrated in FIG. 16.

The SMA actuator 723D is provided with a coil 7235 provided with flanges 7234 on both ends thereof and two SMA coils 7236 arranged around the coil 7235 as illustrated in FIG. 16. The SMA actuator 723D is embedded in a flexible tube portion 72 such that a central axis Ax3 of the coil 7235 (FIG. 16) is identical or parallel to a central axis Ax1 of an insertion unit 7.

The two SMA coils 7236 having the identical structure are arranged so as to be opposed to each other across the coil 7235. The SMA coil 7236 is configured such that a substantial central portion thereof is locked to one flange 7234 and both ends thereof are fixed to the other flange 7234.

The SMA actuator 723D is configured such that the two SMA coils 7236 are energized to be heated by a control device 6 (an operation controller 66) through a signal cable (not illustrated) drawn in a flexible tube portion 72. Herein, the two SMA coils 7236 tend to contract due to energization/heating, but since they are arranged so as to be opposed to each other, the contraction is regulated. Therefore, stiffness (bending rigidity) of the SMA actuator 723D increases as a current value applied increases. That is to say, changing the stiffness of the SMA actuator 723D also changes the bending rigidity of the segment 721 in which the SMA actuator 723D is embedded.

Figure 17A:
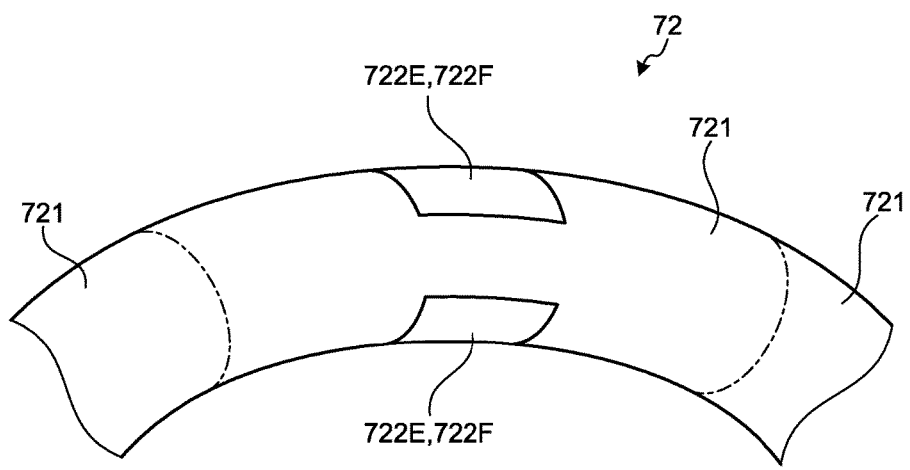
FIG. 17A is a schematic view illustrating a modification of the first to fourth embodiments of the present invention.
Figure 17B:
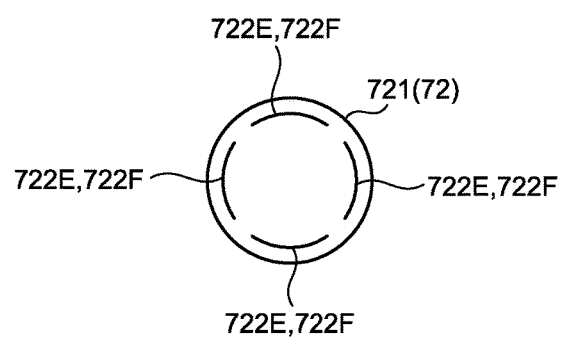
FIG. 17B is a schematic view illustrating the modification of the first to fourth embodiments of the present invention.
Figure 18A:
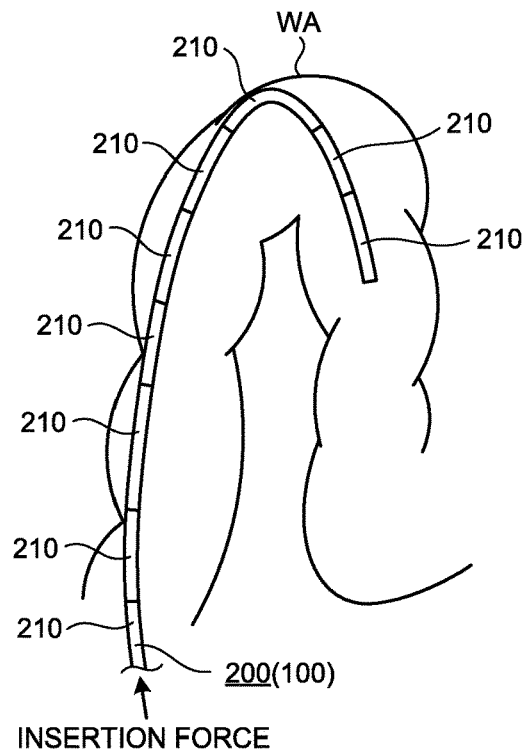
FIG. 18A is a schematic view for illustrating a conventional endoscope device.
Figure 18B:
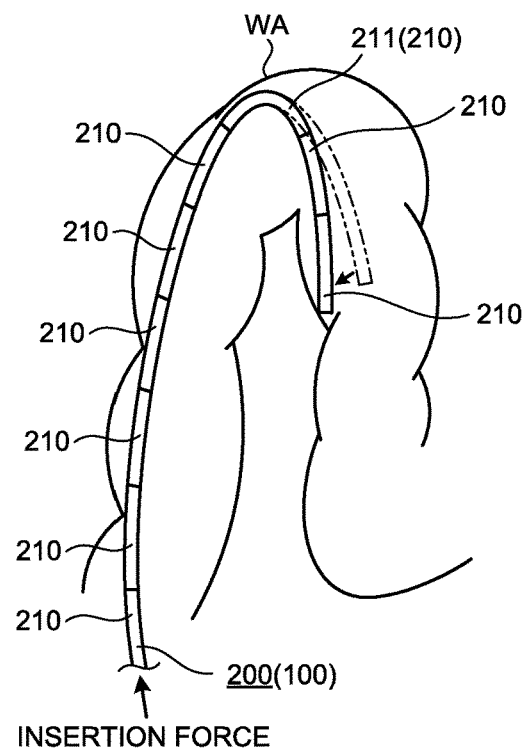
FIG. 18B is a schematic view for illustrating the conventional endoscope device.

FIGS. 17A and 17B are schematic views illustrating a modification of the first to fourth embodiments.

In the above-described first to fourth embodiments, although a plurality of source coils 722 and the antenna 5 are used to calculate the bending angle θ of each of all the segments 721 as the state quantity for each segment 721 based on the detection signal from the antenna 5, different configurations may be employed.

For example, a plurality of pressure detecting units 722E such as capacitance pressure sensors (FIGS. 17A and 17B (a cross-sectional view of the flexible tube portion 72 illustrated in FIG. 17A) which detects pressure from outside on the flexible tube portion 72 to output pressure information indicating the pressure is provided for each of all the segments 721 forming the flexible tube portion 72. For example, four pressure detecting units 722E are provided around each segment 721 as illustrated in FIGS. 17A and 17B. A state quantity calculating unit 63 calculates the pressure from outside (corresponding to drag force DR) of each of all the segments as the above-described state quantity based on a plurality of pieces of pressure information output from a plurality of pressure detecting units 722E. It is also possible to use the pressure information output from the pressure detecting unit 722E directly as the above-described state quantity; in this case, the pressure detecting unit 722E serves as the state quantity calculating unit 63.

For example, a plurality of strain detecting units 722F such as strain gauges (FIGS. 17A and 17B) which detects bending strain by a load from outside on the flexible tube portion 72 to output strain information indicating the bending strain is provided for each of all the segments 721 forming the flexible tube portion 72. For example, four strain detecting units 722F are provided around each segment 721 as illustrated in FIGS. 17A and 17B. The state quantity calculating unit 63 calculates bending strain ε (drag force DR=bending strain ε×Young's modulus E of the flexible tube portion 72) of each segment 721 by the load from the outside as the above-described state quantity based on a plurality of pieces of strain information output from a plurality of strain detecting units 722F. It is also possible to use the strain information output from the strain detecting unit 722F directly as the above-described state quantity; in this case, the strain detecting unit 722F serves as the state quantity calculating unit 63.

Modes (position, number, configuration) of the source coil 722 described in the above-described first to fourth embodiments, the pressure detecting unit 722E, and the strain detecting unit 722F illustrated in FIGS. 17A and 17B described above are not necessarily common among the segments 721, and the modes may be different among the segments 721.

In the above-described first to fourth embodiments, the endoscope devices 1 and 1A to 1C are used not only in the medical field but also in a technical field and they may also be the endoscope devices which observe the inside of a target to be observed such as a machine structure.

In the above-described first to fourth embodiments, although the index value calculating unit 65 adds the state quantity of one segment 721 to the state quantity (bending angle θ) of the segment 721 adjacent to the one segment 721 on the distal end side to calculate the index value according to the one segment 721, different configurations may be employed.

For example, all the state quantities of a predetermined number of (two or more) segments 721 continuously provided on a distal end side of one segment 721 are added to the state quantity of the one segment 721 to calculate the index value according to the one segment 721.

A processing flow is not limited to the processing order in the flowchart described in the above-described first to fourth embodiments and may also be changed in a consistent manner.

Furthermore, an algorithm of the processing described by using the flowchart in this specification may also be described as a program. Such program may be recorded in a recording unit in a computer or in a computer readable recording medium. The program may be recorded in the recording unit or the recording medium when the computer or the recording medium is shipped as a product or may be downloaded through a communication network.

According to some embodiments, when one of a plurality of segments is pressed, for example, the one segment is specified as an origin segment to set a segment range indicating which segment the bending rigidity is to be changed or to set the bending rigidity, among the plurality of segments. The endoscope device sets the segment range or the bending rigidity described above based on the origin segment and decreases the bending rigidity of two or more continuously provided segments among the plurality of segments based on the set segment range or the set bending rigidity.

Therefore, when an insertion unit is inserted into a lumen and if a certain segment abuts on a bent portion of the lumen, the bending rigidity of the two or more continuously provided segments decreases and bending amounts of the two or more continuously provided segments increase, which deforms the entire insertion unit to be an obtuse-angled shape. That is to say, the obtuse-angled shaped insertion unit is brought into contact with a wall of the lumen, and pressure applied from the wall of the lumen also becomes small. Therefore, when insertion force is applied to the insertion unit, the insertion force is not converted into force to push the wall of the lumen but is effectively utilized as force to advance a distal end of the insertion unit to facilitate passage through the bent portion of the lumen.

With this feature, it is possible to facilitate the insertion of the insertion unit into the lumen and to improve operability.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope device comprising:
   an insertion unit comprising a plurality of segments continuously provided along an axial direction of the insertion unit and configured to be inserted into a lumen;
   a plurality of variable rigidity actuators, wherein each of the plurality of variable rigidity actuators is provided for a corresponding one of the plurality of segments, wherein the each of the plurality of variable rigidity actuators is configured to be operated to vary bending rigidity of the corresponding one of the plurality of segments; and a processor comprising hardware, wherein the processor is configured to:
calculate a state quantity indicating a state of each of the plurality of segments;
specify an origin segment among the plurality of segments in setting a segment range indicating which segment the bending rigidity is to be changed or in setting the bending rigidity, based on the state quantity of each of the plurality of segments;
set the segment range indicating which segment the bending rigidity is to be changed among the plurality of segments or set the bending rigidity of each of the plurality of segments, based on the origin segment; and
decrease bending rigidities of two or more continuously provided segments among the plurality of segments based on the set segment range or on the set bending rigidity.

2. The endoscope device according to claim 1, wherein the processor is configured to:
set the segment range including the origin segment or including a segment away from the origin segment by a predetermined number of segments; and
decrease the bending rigidity of each segment within the segment range.

3. The endoscope device according to claim 1, wherein the processor is configured to cause the bending rigidity of the origin segment or of a segment away from the origin segment by a predetermined number of segments to be lowest.

4. The endoscope device according to claim 1, wherein the two or more continuously provided segments are a predetermined number of segments continuously provided from the origin segment toward a proximal end side of the insertion unit, among the plurality of segments.

5. The endoscope device according to claim 1, wherein the processor is configured to cause the bending rigidity of a segment adjacent to the origin segment to be lowest.

6. The endoscope device according to claim 1, wherein as the state quantity of one segment of the plurality of segments increases, the processor is configured to decrease the bending rigidity of the one segment or of a segment away from the one segment by a predetermined number of segments.

7. The endoscope device according to claim 1, wherein if an index value based on the state quantity of one segment of the plurality of segments is larger than a predetermined threshold, the processor is configured to decrease the bending rigidity of the one segment or of a segment away from the one segment by a predetermined number of segments.

8. The endoscope device according to claim 1, wherein in decreasing the bending rigidities of the two or more continuously provided segments, the processor is configured to decrease the bending rigidity of one segment of the two or more continuously provided segments, based on the state quantity of a segment adjacent to the one segment on a distal end side of the insertion unit.

9. The endoscope device according to claim 8, wherein the processor is configured to:
calculate index values for changing the bending rigidities of the two or more continuously provided segments;
in calculating the index values, calculate an index value for changing the bending rigidity of the one segment by adding the state quantity of the one segment to the state quantity of the segment adjacent to the one segment on the distal end side; and
change the bending rigidities of the two or more continuously provided segments based on the index values.

10. The endoscope device according to claim 1, wherein the processor is configured to specify, as the origin segment, a segment having the largest state quantity among the plurality of segments.

11. The endoscope device according to claim 1, wherein the processor is configured to operate the plurality of variable rigidity actuators portions when one of state quantities of the plurality of segments is equal to or larger than a predetermined threshold.

12. The endoscope device according to claim 1, further comprising a plurality of position detecting circuits provided on the insertion unit along the axial direction and configured to output a plurality of pieces of positional information,
wherein the processor is configured to calculate a bending angle of each of the plurality of segments as the state quantity for each of the plurality of segments, based on the plurality of pieces of positional information output from the plurality of position detecting circuits.

13. The endoscope device according to claim 1, wherein the processor is configured to:
calculate amounts of resistance force caused by friction of the plurality of segments based on the state quantity for each of the plurality of segments; and
integrate the amounts of the resistance force in order from a segment on a most proximal end side of the plurality of segments to obtain an integrated value,
wherein when the integrated value obtained is equal to or larger than a predetermined threshold, the processor is configured to specify, as the origin segment, a segment having an amount of resistance force integrated last.

14. The endoscope device according to claim 1, further comprising a plurality of pressure detecting sensors provided on the insertion unit along the axial direction and configured to detect pressure from outside on the insertion unit and to output a plurality of pieces of pressure information indicating the pressure,
wherein the processor is configured to calculate the pressure from outside for each of the plurality of segments as the state quantity for each of the plurality of segments, based on the plurality of pieces of pressure information output from the plurality of pressure detecting sensors.

15. The endoscope device according to claim 1, further comprising a plurality of strain gauges provided on the insertion unit along the axial direction and configured to detect bending strain caused by a load from outside on the insertion unit and to output a plurality of pieces of strain information indicating the bending strain,
wherein the processor is configured to calculate the bending strain caused by the load from outside for each of the plurality of segments as the state quantity for each of the plurality of segments, based on the plurality of pieces of strain information output from the plurality of strain gauges.

16. The endoscope device according to claim 1, wherein the plurality of variable rigidity actuators is configured to change bending rigidities of all of the plurality of segments.

17. The endoscope device according to claim 1, wherein the processor is configured to:
predict whether the insertion unit is put into a stuck state in which propulsion in a distal end direction of the insertion unit is lost, based on the state quantity for each of the plurality of segments; and
operate the plurality of variable rigidity actuators when the processor predicts that the insertion unit is put into the stuck state.

18. The endoscope device according to claim 17, wherein the processor is configured to:
calculate amounts of resistance force caused by friction of the plurality of segments based on the state quantity for each of the plurality of segments;
calculate a sum of the amounts of the resistance force of all the plurality of segments; and
predict that the insertion unit is put into the stuck state when the sum is equal to or larger than a predetermined threshold.

19. A method for operating an endoscope device, the endoscope device comprising: an insertion unit comprising a plurality of segments continuously provided along an axial direction of the insertion unit and configured to be inserted into a lumen; and a plurality of variable rigidity actuators, wherein each of the plurality of variable rigidity actuators is provided for a corresponding one of the plurality of segments, wherein the each of the plurality of variable rigidity actuators is configured to be operated to vary bending rigidity of the corresponding one of the plurality of segments, the method comprising:
calculating a state quantity indicating a state of each of the plurality of segments;
specifying an origin segment among the plurality of segments in setting a segment range indicating which segment the bending rigidity is to be changed or in setting the bending rigidity, based on the state quantity of each of the plurality of segments;
setting the segment range indicating which segment the bending rigidity is to be changed among the plurality of segments, or setting the bending rigidity of each of the plurality of segments, based on the origin segment; and
decreasing bending rigidities of two or more continuously provided segments among the plurality of segments based on the set segment range or on the set bending rigidity.

20. A non-transitory computer-readable recording medium with an executable program stored thereon for operating an endoscope device, the endoscope device comprising: an insertion unit comprising a plurality of segments continuously provided along an axial direction of the insertion unit and configured to be inserted into a lumen; and a plurality of variable rigidity actuators, wherein each of the plurality of variable rigidity actuators is provided for a corresponding one of the plurality of segments, wherein the each of the plurality of variable rigidity actuators is configured to be operated to vary bending rigidity of the corresponding one of the plurality of segments, wherein the program causes a computer to at least:
calculate a state quantity indicating a state of each of the plurality of segments;
specify an origin segment among the plurality of segments in setting a segment range indicating which segment the bending rigidity is to be changed or in setting the bending rigidity, based on the state quantity of each of the plurality of segments;
set the segment range indicating which segment the bending rigidity is to be changed among the plurality of segments, or setting the bending rigidity of each of the plurality of segments, based on the origin segment; and
decrease bending rigidities of two or more continuously provided segments among the plurality of segments based on the set segment range or on the set bending rigidity.

\* \* \* \* \*